(12) United States Patent
Morin et al.

(10) Patent No.: US 10,028,831 B2
(45) Date of Patent: Jul. 24, 2018

(54) TRANSCATHETER VALVE WITH PARAVALVULAR LEAK SEALING RING

(71) Applicant: St. Jude Medical, Cardiology Division, Inc., St. Paul, MN (US)

(72) Inventors: Kristen T. Morin, Saint Paul, MN (US); Andrea N. Para, St. Louis, MO (US); Peter N. Braido, Wyoming, MN (US); Sounthara Khouengboua, Chaska, MN (US); Thomas M. Benson, Minneapolis, MN (US); Saravana B. Kumar, Minnetonka, MN (US); Bruce Moseman, Belle Plaine, MN (US); Gaurav Satam, Falcon Heights, MN (US)

(73) Assignee: St. Jude Medical, Cardiology Division, Inc., St. Paul, MN (US)

( * ) Notice: Subject to any disclaimer, the term of this patent is extended or adjusted under 35 U.S.C. 154(b) by 0 days.

(21) Appl. No.: 15/586,595

(22) Filed: May 4, 2017

(65) Prior Publication Data
US 2017/0231764 A1     Aug. 17, 2017

Related U.S. Application Data

(63) Continuation of application No. 14/709,560, filed on May 12, 2015, now Pat. No. 9,668,858.
(Continued)

(51) Int. Cl.
*A61F 2/24*     (2006.01)

(52) U.S. Cl.
CPC .......... *A61F 2/2436* (2013.01); *A61F 2/2418* (2013.01); *A61F 2/2472* (2013.01);
(Continued)

(58) Field of Classification Search
CPC ......... A61F 2/24; A61F 2/2418; A61F 2/2403
(Continued)

(56) References Cited

U.S. PATENT DOCUMENTS

| | | | |
|---|---|---|---|
| 3,564,617 A | * | 2/1971 | Sauvage et al. ...... A61F 2/2409 623/2.4 |
| 3,657,744 A | | 4/1972 | Ersek |

(Continued)

FOREIGN PATENT DOCUMENTS

| | | |
|---|---|---|
| CN | 103705315 A | 4/2014 |
| DE | 19857887 A1 | 7/2000 |

(Continued)

OTHER PUBLICATIONS

Buellesfeld et al., Treatment of paravalvular leaks through inverventional techniques; Department of Cardiology, Ben University Hospital 2011.
(Continued)

*Primary Examiner* — Suzette J Gherbi
(74) *Attorney, Agent, or Firm* — Lerner, David, Littenberg, Krumholz & Mentlik, LLP

(57) ABSTRACT

A prosthetic heart valve includes a collapsible and expandable stent extending from an inflow end to an outflow end and a plurality of prosthetic valve leaflets coupled to the stent. The prosthetic heart valve may also include a sealing ring coupled to the inflow end of the stent, the sealing ring comprising a tube extending circumferentially around the inflow end of the stent. The tube may be formed from a wire coiled into a repeating shape, such as a rectangle or a diamond, so that the tube is collapsible. A covering may at least partially surround the tube. The sealing ring may include a first filler positioned within the tube and/or a second filler positioned between the tube and the covering.

20 Claims, 19 Drawing Sheets

Related U.S. Application Data

(60) Provisional application No. 61/994,253, filed on May 16, 2014.

(52) U.S. Cl.
CPC .............. *A61F 2210/0014* (2013.01); *A61F 2220/0075* (2013.01); *A61F 2230/0017* (2013.01); *A61F 2230/0019* (2013.01); *A61F 2250/0069* (2013.01)

(58) Field of Classification Search
USPC ................................................ 623/2.1–2.19
See application file for complete search history.

(56) References Cited

U.S. PATENT DOCUMENTS

| | | |
|---|---|---|
| 4,275,469 A | 6/1981 | Gabbay |
| 4,491,986 A | 1/1985 | Gabbay |
| 4,759,758 A | 7/1988 | Gabbay |
| 4,878,906 A | 11/1989 | Lindemann et al. |
| 4,922,905 A | 5/1990 | Strecker |
| 4,994,077 A | 2/1991 | Dobben |
| 5,411,552 A | 5/1995 | Andersen et al. |
| 5,480,423 A | 1/1996 | Ravenscroft et al. |
| 5,843,167 A | 12/1998 | Dwyer et al. |
| 5,855,601 A | 1/1999 | Bessler et al. |
| 5,935,163 A | 8/1999 | Gabbay |
| 5,961,549 A | 10/1999 | Nguyen et al. |
| 6,045,576 A | 4/2000 | Starr et al. |
| 6,077,297 A | 6/2000 | Robinson et al. |
| 6,083,257 A | 7/2000 | Taylor et al. |
| 6,090,140 A | 7/2000 | Gabbay |
| 6,214,036 B1 | 4/2001 | Letendre et al. |
| 6,264,691 B1 | 7/2001 | Gabbay |
| 6,267,783 B1 | 7/2001 | Letendre et al. |
| 6,368,348 B1 | 4/2002 | Gabbay |
| 6,419,695 B1 | 7/2002 | Gabbay |
| 6,468,660 B2 | 10/2002 | Ogle et al. |
| 6,488,702 B1 | 12/2002 | Besselink |
| 6,517,576 B2 | 2/2003 | Gabbay |
| 6,533,810 B2 | 3/2003 | Hankh et al. |
| 6,582,464 B2 | 6/2003 | Gabbay |
| 6,610,088 B1 | 8/2003 | Gabbay |
| 6,623,518 B2 | 9/2003 | Thompson et al. |
| 6,652,578 B2 | 11/2003 | Bailey et al. |
| 6,685,625 B2 | 2/2004 | Gabbay |
| 6,716,244 B2 | 4/2004 | Klaco |
| 6,719,789 B2 | 4/2004 | Cox |
| 6,730,118 B2 | 5/2004 | Spenser et al. |
| 6,783,556 B1 | 8/2004 | Gabbay |
| 6,790,230 B2 | 9/2004 | Beyersdorf et al. |
| 6,814,746 B2 | 11/2004 | Thompson et al. |
| 6,830,584 B1 | 12/2004 | Seguin |
| 6,869,444 B2 | 3/2005 | Gabbay |
| 6,893,460 B2 | 5/2005 | Spenser et al. |
| 6,908,481 B2 | 6/2005 | Cribier |
| 6,951,573 B1 | 10/2005 | Dilling |
| 7,018,406 B2 | 3/2006 | Seguin et al. |
| 7,025,780 B2 | 4/2006 | Gabbay |
| 7,137,184 B2 | 11/2006 | Schreck |
| 7,160,322 B2 | 1/2007 | Gabbay |
| 7,195,641 B2 | 3/2007 | Palmaz et al. |
| 7,247,167 B2 | 7/2007 | Gabbay |
| 7,267,686 B2 | 9/2007 | DiMatteo et al. |
| 7,276,078 B2 | 10/2007 | Spenser et al. |
| 7,311,730 B2 | 12/2007 | Gabbay |
| 7,320,704 B2 | 1/2008 | Lashinski et al. |
| 7,329,278 B2 | 2/2008 | Seguin et al. |
| 7,374,573 B2 | 5/2008 | Gabbay |
| 7,381,218 B2 | 6/2008 | Schreck |
| 7,381,219 B2 | 6/2008 | Salahieh et al. |
| 7,452,371 B2 | 11/2008 | Pavcnik et al. |
| 7,510,572 B2 | 3/2009 | Gabbay |
| 7,510,575 B2 | 3/2009 | Spenser et al. |
| 7,524,331 B2 | 4/2009 | Birdsall |
| 7,534,261 B2 | 5/2009 | Friedman |
| RE40,816 E | 6/2009 | Taylor et al. |
| 7,585,321 B2 | 9/2009 | Cribier |
| 7,628,805 B2 | 12/2009 | Spenser et al. |
| 7,682,390 B2 | 3/2010 | Seguin |
| 7,708,775 B2 | 5/2010 | Rowe et al. |
| 7,731,742 B2 | 6/2010 | Schlick et al. |
| 7,748,389 B2 | 7/2010 | Salahieh et al. |
| 7,780,725 B2 | 8/2010 | Haug et al. |
| 7,799,069 B2 | 9/2010 | Bailey et al. |
| 7,803,185 B2 | 9/2010 | Gabbay |
| 7,824,442 B2 | 11/2010 | Salahieh et al. |
| 7,837,727 B2 | 11/2010 | Goetz et al. |
| 7,846,203 B2 | 12/2010 | Cribier |
| 7,846,204 B2 | 12/2010 | Letac et al. |
| 7,892,281 B2 | 2/2011 | Seguin et al. |
| 7,914,569 B2 | 3/2011 | Nguyen et al. |
| 7,959,666 B2 | 6/2011 | Salahieh et al. |
| 7,959,672 B2 | 6/2011 | Salahieh et al. |
| 7,972,378 B2 | 7/2011 | Tabor et al. |
| 7,988,724 B2 | 8/2011 | Salahieh et al. |
| 7,993,394 B2 | 8/2011 | Hariton et al. |
| 8,016,877 B2 | 9/2011 | Seguin et al. |
| D648,854 S | 11/2011 | Braido |
| 8,048,153 B2 | 11/2011 | Salahieh et al. |
| 8,052,741 B2 | 11/2011 | Bruszewski et al. |
| 8,052,749 B2 | 11/2011 | Salahieh et al. |
| 8,052,750 B2 | 11/2011 | Tuval et al. |
| 8,062,355 B2 | 11/2011 | Figulla et al. |
| 8,075,611 B2 | 12/2011 | Millwee et al. |
| D652,926 S | 1/2012 | Braido |
| D652,927 S | 1/2012 | Braido et al. |
| D653,341 S | 1/2012 | Braido et al. |
| D653,342 S | 1/2012 | Braido et al. |
| D653,343 S | 1/2012 | Ness et al. |
| D654,169 S | 2/2012 | Braido |
| D654,170 S | 2/2012 | Braido et al. |
| 8,137,398 B2 | 3/2012 | Tuval et al. |
| 8,142,497 B2 | 3/2012 | Friedman |
| D660,432 S | 5/2012 | Braido |
| D660,433 S | 5/2012 | Braido et al. |
| D660,967 S | 5/2012 | Braido et al. |
| 8,182,528 B2 | 5/2012 | Salahieh et al. |
| 8,221,493 B2 | 7/2012 | Boyle et al. |
| 8,230,717 B2 | 7/2012 | Matonick |
| 8,231,670 B2 | 7/2012 | Salahieh et al. |
| 8,252,051 B2 | 8/2012 | Chau et al. |
| 8,308,798 B2 | 11/2012 | Pintor et al. |
| 8,313,525 B2 | 11/2012 | Tuval et al. |
| 8,323,335 B2 | 12/2012 | Rowe et al. |
| 8,323,336 B2 | 12/2012 | Hill et al. |
| 8,343,213 B2 | 1/2013 | Salahieh et al. |
| 8,348,995 B2 | 1/2013 | Tuval et al. |
| 8,348,996 B2 | 1/2013 | Tuval et al. |
| 8,348,998 B2 | 1/2013 | Pintor et al. |
| 8,366,769 B2 | 2/2013 | Huynh et al. |
| 8,403,983 B2 | 3/2013 | Quadri et al. |
| 8,408,214 B2 | 4/2013 | Spenser |
| 8,414,643 B2 | 4/2013 | Tuval et al. |
| 8,425,593 B2 | 4/2013 | Braido et al. |
| 8,449,599 B2 | 5/2013 | Chau et al. |
| 8,449,604 B2 | 5/2013 | Moaddeb et al. |
| 8,454,686 B2 | 6/2013 | Alkhatib |
| 8,500,798 B2 | 8/2013 | Rowe et al. |
| 8,568,474 B2 | 10/2013 | Yeung et al. |
| 8,579,962 B2 | 11/2013 | Salahieh et al. |
| 8,579,966 B2 | 11/2013 | Seguin et al. |
| 8,585,755 B2 | 11/2013 | Chau et al. |
| 8,591,575 B2 | 11/2013 | Cribier |
| 8,597,349 B2 | 12/2013 | Alkhatib |
| 8,603,159 B2 | 12/2013 | Seguin et al. |
| 8,603,160 B2 | 12/2013 | Salahieh et al. |
| 8,613,765 B2 | 12/2013 | Bonhoeffer et al. |
| 8,623,074 B2 | 1/2014 | Ryan |
| 8,652,204 B2 | 2/2014 | Quill et al. |
| 8,663,322 B2 | 3/2014 | Keranen |
| 8,668,733 B2 | 3/2014 | Haug et al. |
| 8,685,080 B2 | 4/2014 | White |

(56) References Cited

U.S. PATENT DOCUMENTS

| | | |
|---|---|---|
| 8,728,154 B2 | 5/2014 | Alkhatib |
| 8,747,459 B2 | 6/2014 | Nguyen et al. |
| 8,764,820 B2 | 7/2014 | Dehdashtian et al. |
| 8,795,357 B2 | 8/2014 | Yohanan et al. |
| 8,801,776 B2 | 8/2014 | House et al. |
| 8,808,356 B2 | 8/2014 | Braido et al. |
| 8,828,078 B2 | 9/2014 | Salahieh et al. |
| 8,834,563 B2 | 9/2014 | Righini |
| 8,840,663 B2 | 9/2014 | Salahieh et al. |
| 8,876,894 B2 | 11/2014 | Tuval et al. |
| 8,876,895 B2 | 11/2014 | Tuval et al. |
| 8,940,040 B2 | 1/2015 | Shahriari |
| 8,945,209 B2 | 2/2015 | Bonyuet et al. |
| 8,961,595 B2 | 2/2015 | Alkhatib |
| 8,974,523 B2 | 3/2015 | Thill et al. |
| 8,974,524 B2 | 3/2015 | Yeung et al. |
| 2002/0036220 A1 | 3/2002 | Gabbay |
| 2003/0023303 A1 | 1/2003 | Palmaz et al. |
| 2003/0050694 A1 | 3/2003 | Yang et al. |
| 2003/0130726 A1 | 7/2003 | Thorpe et al. |
| 2004/0049262 A1 | 3/2004 | Obermiller et al. |
| 2004/0093075 A1 | 5/2004 | Kuehne |
| 2004/0111111 A1 | 6/2004 | Lin |
| 2004/0210304 A1 | 10/2004 | Seguin et al. |
| 2004/0260389 A1 | 12/2004 | Case et al. |
| 2005/0096726 A1 | 5/2005 | Sequin et al. |
| 2005/0137682 A1 | 6/2005 | Justino |
| 2005/0137695 A1 | 6/2005 | Salahieh et al. |
| 2005/0137697 A1 | 6/2005 | Salahieh et al. |
| 2005/0203605 A1 | 9/2005 | Dolan |
| 2005/0256566 A1 | 11/2005 | Gabbay |
| 2006/0008497 A1 | 1/2006 | Gabbay |
| 2006/0074484 A1 | 4/2006 | Huber |
| 2006/0122692 A1 | 6/2006 | Gilad et al. |
| 2006/0144614 A1* | 7/2006 | Kircanski ............ F01N 3/2853 174/117 M |
| 2006/0149360 A1 | 7/2006 | Schwammenthal et al. |
| 2006/0161249 A1 | 7/2006 | Realyvasquez et al. |
| 2006/0173532 A1 | 8/2006 | Flagle et al. |
| 2006/0178740 A1 | 8/2006 | Stacchino et al. |
| 2006/0206202 A1 | 9/2006 | Bonhoeffer et al. |
| 2006/0241744 A1 | 10/2006 | Beith |
| 2006/0241745 A1 | 10/2006 | Solem |
| 2006/0259120 A1 | 11/2006 | Vongphakdy et al. |
| 2006/0259137 A1 | 11/2006 | Artof et al. |
| 2006/0265056 A1 | 11/2006 | Nguyen et al. |
| 2006/0276813 A1 | 12/2006 | Greenberg |
| 2006/0276874 A1 | 12/2006 | Wilson et al. |
| 2007/0010876 A1 | 1/2007 | Salahieh et al. |
| 2007/0027534 A1 | 2/2007 | Bergheim et al. |
| 2007/0043435 A1 | 2/2007 | Seguin et al. |
| 2007/0055358 A1 | 3/2007 | Krolik et al. |
| 2007/0067029 A1 | 3/2007 | Gabbay |
| 2007/0093890 A1 | 4/2007 | Eliasen et al. |
| 2007/0100435 A1 | 5/2007 | Case et al. |
| 2007/0118210 A1 | 5/2007 | Pinchuk |
| 2007/0213813 A1 | 9/2007 | Von Segesser et al. |
| 2007/0233228 A1 | 10/2007 | Eberhardt et al. |
| 2007/0244545 A1 | 10/2007 | Birdsall et al. |
| 2007/0244552 A1 | 10/2007 | Salahieh et al. |
| 2007/0288087 A1 | 12/2007 | Fearnot et al. |
| 2008/0021552 A1 | 1/2008 | Gabbay |
| 2008/0039934 A1 | 2/2008 | Styrc |
| 2008/0071369 A1 | 3/2008 | Tuval et al. |
| 2008/0082164 A1 | 4/2008 | Friedman |
| 2008/0097595 A1 | 4/2008 | Gabbay |
| 2008/0114452 A1 | 5/2008 | Gabbay |
| 2008/0125853 A1 | 5/2008 | Bailey et al. |
| 2008/0140189 A1 | 6/2008 | Nguyen et al. |
| 2008/0147183 A1 | 6/2008 | Styrc |
| 2008/0154355 A1 | 6/2008 | Benichou et al. |
| 2008/0154356 A1 | 6/2008 | Obermiller et al. |
| 2008/0243245 A1 | 10/2008 | Thambar et al. |
| 2008/0255662 A1 | 10/2008 | Stacchino et al. |
| 2008/0262602 A1 | 10/2008 | Wilk et al. |
| 2008/0269879 A1 | 10/2008 | Sathe et al. |
| 2009/0099653 A1 | 4/2009 | Suri et al. |
| 2009/0112309 A1 | 4/2009 | Jaramillo et al. |
| 2009/0138079 A1 | 5/2009 | Tuval et al. |
| 2009/0276027 A1 | 11/2009 | Glynn |
| 2010/0004740 A1 | 1/2010 | Seguin et al. |
| 2010/0036484 A1 | 2/2010 | Hariton et al. |
| 2010/0049306 A1 | 2/2010 | House et al. |
| 2010/0087907 A1 | 4/2010 | Lattouf |
| 2010/0131055 A1 | 5/2010 | Case et al. |
| 2010/0168778 A1 | 7/2010 | Braido |
| 2010/0168839 A1 | 7/2010 | Braido et al. |
| 2010/0168844 A1 | 7/2010 | Toomes et al. |
| 2010/0185277 A1 | 7/2010 | Braido et al. |
| 2010/0191326 A1 | 7/2010 | Alkhatib |
| 2010/0204781 A1 | 8/2010 | Alkhatib |
| 2010/0204785 A1 | 8/2010 | Alkhatib |
| 2010/0217382 A1 | 8/2010 | Chau et al. |
| 2010/0234940 A1 | 9/2010 | Dolan |
| 2010/0249911 A1 | 9/2010 | Alkhatib |
| 2010/0249923 A1 | 9/2010 | Alkhatib et al. |
| 2010/0286768 A1 | 11/2010 | Alkhatib |
| 2010/0298931 A1 | 11/2010 | Quadri et al. |
| 2011/0029072 A1 | 2/2011 | Gabbay |
| 2011/0054466 A1 | 3/2011 | Rothstein et al. |
| 2011/0054598 A1* | 3/2011 | Johnson ............... A61F 2/2409 623/2.41 |
| 2011/0098800 A1 | 4/2011 | Braido et al. |
| 2011/0098802 A1 | 4/2011 | Braido et al. |
| 2011/0137397 A1 | 6/2011 | Chau et al. |
| 2011/0172765 A1 | 7/2011 | Nguyen et al. |
| 2011/0208283 A1 | 8/2011 | Rust |
| 2011/0264206 A1 | 10/2011 | Tabor |
| 2012/0035722 A1 | 2/2012 | Tuval |
| 2012/0078347 A1 | 3/2012 | Braido et al. |
| 2012/0101572 A1 | 4/2012 | Kovalsky et al. |
| 2012/0123529 A1 | 5/2012 | Levi et al. |
| 2012/0303116 A1 | 11/2012 | Gorman, III et al. |
| 2013/0274873 A1 | 10/2013 | Delaloye et al. |
| 2013/0331929 A1 | 12/2013 | Mitra et al. |
| 2014/0114402 A1* | 4/2014 | Ahlberg ............... A61F 2/2418 623/2.11 |
| 2014/0121763 A1 | 5/2014 | Duffy et al. |
| 2014/0155997 A1 | 6/2014 | Braido |
| 2014/0214159 A1 | 7/2014 | Vidlund et al. |
| 2014/0228946 A1 | 8/2014 | Chau et al. |
| 2014/0303719 A1 | 10/2014 | Cox et al. |
| 2014/0324164 A1 | 10/2014 | Gross et al. |
| 2014/0343671 A1 | 11/2014 | Yohanan et al. |
| 2014/0350668 A1 | 11/2014 | Delaloye et al. |
| 2014/0350669 A1 | 11/2014 | Gillespie et al. |
| 2014/0364943 A1* | 12/2014 | Conklin ............... A61F 2/2412 623/2.11 |
| 2014/0371844 A1* | 12/2014 | Dale ..................... A61F 2/2418 623/2.11 |
| 2015/0157455 A1* | 6/2015 | Hoang .................. A61F 2/2418 623/2.18 |
| 2015/0209136 A1* | 7/2015 | Braido ................. A61F 2/2403 623/2.18 |
| 2015/0351905 A1* | 12/2015 | Khouengboua ....... A61F 2/2412 623/2.18 |
| 2015/0366664 A1* | 12/2015 | Guttenberg ........... A61F 2/2409 623/2.17 |
| 2016/0106538 A1* | 4/2016 | Mitra ..................... A61L 31/145 623/1.11 |
| 2016/0120646 A1* | 5/2016 | Dwork .................. A61F 2/2469 623/2.18 |
| 2016/0143732 A1* | 5/2016 | Glimsdale ............ A61F 2/2418 623/2.41 |
| 2016/0151153 A1* | 6/2016 | Sandstrom ........... A61F 2/2418 623/2.18 |
| 2016/0213468 A1* | 7/2016 | Braido ................. A61F 2/2412 |
| 2016/0317291 A1 | 11/2016 | Bishop et al. |

FOREIGN PATENT DOCUMENTS

| | | |
|---|---|---|
| DE | 10121210 A1 | 11/2002 |
| DE | 202008009610 U1 | 12/2008 |

(56) References Cited

FOREIGN PATENT DOCUMENTS

| | | | |
|---|---|---|---|
| EP | 0850607 | A1 | 7/1998 |
| EP | 1000590 | A1 | 5/2000 |
| EP | 1360942 | A1 | 11/2003 |
| EP | 1584306 | A1 | 10/2005 |
| EP | 1598031 | A2 | 11/2005 |
| EP | 1926455 | A2 | 6/2008 |
| EP | 2537487 | A1 | 12/2012 |
| FR | 2850008 | A1 | 7/2004 |
| FR | 2847800 | B1 | 10/2005 |
| WO | 9117720 | A1 | 11/1991 |
| WO | 9716133 | A1 | 5/1997 |
| WO | 9832412 | A2 | 7/1998 |
| WO | 9913801 | A1 | 3/1999 |
| WO | 0128459 | A1 | 4/2001 |
| WO | 0149213 | A2 | 7/2001 |
| WO | 0154625 | A1 | 8/2001 |
| WO | 0156500 | A2 | 8/2001 |
| WO | 0176510 | A2 | 10/2001 |
| WO | 0236048 | A1 | 5/2002 |
| WO | 0247575 | A2 | 6/2002 |
| WO | 03047468 | A1 | 6/2003 |
| WO | 06073626 | A2 | 7/2006 |
| WO | 07071436 | A2 | 6/2007 |
| WO | 08070797 | A2 | 6/2008 |
| WO | 2010008548 | A2 | 1/2010 |
| WO | 2010008549 | A1 | 1/2010 |
| WO | 2010096176 | A1 | 8/2010 |
| WO | 2010098857 | A1 | 9/2010 |
| WO | 2011146759 | A2 | 11/2011 |
| WO | 2014121042 | A1 | 8/2014 |
| WO | 2015023862 | A2 | 2/2015 |

OTHER PUBLICATIONS

De Cisco, Giuseppe, et al. "Aortic valve periprosthetic leakage: anatomic observations and surgical results." The Annals of thoracic surgery 79.5 (2005): 1480-1485.
Gössl, Mario, and Charanjit S. Rihal. "Percutaneous treatment of aortic and mitral valve paravalvular regurgitation." Current cardiology reports 15.8 (2013): 1-8.
Hourihan, Maribeth et al., Transcatheter Umbrella Closure of Valvular and Paravalvular Leaks, Hourihan et al., Journal of the American College of Cardiology, vol. 20, No. 6, pp. 1371-1377, (1992).
International Search Report and Written Opinion for Application No. PCT/US2015/030250 dated Jul. 17, 2015.
Knudsen, L.L. et al., Catheter-implanted prosthetic heart valves, The International Journal of Artificial Organs, vol. 16, No. 5 1993, pp. 253-262.
Muñoz, Daniel Rodríguez, Carla Lázaro Rivera, and José Luis Zamorano Gómez. "Guidance of treatment of perivalvular prosthetic leaks." Current cardiology reports 16.1 (2014): 1-6.
Quaden, René et al., "Percutaneous aortic valve replacement: resection before implantation," 836-840, European J. of Cardio-thoracic Surgery 27 (2005).
Rohde, I., Masch, J.-M., Theisen-Kunde, D., Marczynski-Bühlow, M., Bombien Quaden, R., Lutter, G. and Brinkmann, R. (2015), Resection of Calcified Aortic Heart Leaflets in Vitro by Q-Switched 2 μm Microsecond Laser Radiation. Journal of Cardiac Surgery, 30: 157-162. doi:10.1111/jocs.12481.
Ruiz, Carlos, "Overview of PRE-CE Mark Transcatheter Aortic Valve Technologies", Euro PCR, May 25, 2010.
Swiatkiewicz, Iwona, et al. "Percutaneous closure of mitral perivalvular leak." Kardiologia polska 67.7 (2009): 762.
Technology Frontier, "Heart repairs without surgery. Minimally invasive procedures aim to correct valve leakage", Heart Advisor/Sep. 2004, PubMed ID 15586429.
Transluminal Aortic Valve Placement, Moazami, Nader, et al., ASAIO Journal, 1996; 42:M381-M385.
U.S. Appl. No. 29/375,243, filed Sep. 20, 2010.
U.S. Appl. No. 29/375,260, filed Sep. 20, 2010.
Zegdi, Rachid, MD, PhD et al., "Is It Reasonable to Treat All Calcified Stenotic Aortic Valves With a Valved Stent?" 579-584, J. of the American College of Cardiology, vol. 51, No. 5, Feb. 5, 2008.
Andersen, H. R. et al, Transluminal implantation of artificial heart valves, European Heart Journal (1992) 13, 704-708.
Andersen, Henning Rud, Transluminal Catheter Implanted Prosthetic Heart Valves, International Journal of Angiology 7:102-106 (1998).

* cited by examiner

TRANSCATHETER VALVE WITH PARAVALVULAR LEAK SEALING RING

CROSS-REFERENCE TO RELATED APPLICATIONS

This application is a continuation of U.S. patent application Ser. No. 14/709,560 filed May 12, 2015 which claims the benefit of the filing date of U.S. Provisional Patent Application No. 61/994,253, filed May 16, 2014, the disclosures of which are both hereby incorporated by reference herein.

BACKGROUND

The present disclosure relates to heart valve replacement and, in particular, to collapsible prosthetic heart valves. More particularly, the present disclosure relates to collapsible prosthetic transcatheter heart valves which minimize or reduce para valvular leaks.

Prosthetic heart valves that are collapsible to a relatively small circumferential size can be delivered into a patient less invasively than valves that are not collapsible. For example, a collapsible valve may be delivered into a patient via a tube-like delivery apparatus such as a catheter, a trocar, a laparoscopic instrument, or the like. This collapsibility can avoid the need for a more invasive procedure such as full open-chest, open-heart surgery.

Collapsible prosthetic heart valves typically take the form of a valve structure mounted on a stent. There are two common types of stents on which the valve structures are ordinarily mounted: a self-expanding stent and a balloon-expandable stent. To place such valves into a delivery apparatus and ultimately into a patient, the valve is first collapsed or crimped to reduce its circumferential size.

When a collapsed prosthetic valve has reached the desired implant site in the patient (e.g., at or near the annulus of the patient's heart valve that is to be replaced by the prosthetic valve), the prosthetic valve can be deployed or released from the delivery apparatus and re-expanded to full operating size. For balloon-expandable valves, this generally involves releasing the valve, assuring its proper location, and then expanding a balloon positioned within the valve stent. For self-expanding valves, on the other hand, the stent automatically expands as a sheath covering the valve is withdrawn.

After implantation, imperfect sealing between the cuff and the site of implant may cause complications such as para valvular leakage ("PV leak"), or blood flowing through a channel between the structure of the implanted valve and cardiac tissue as a result of the imperfect sealing.

BRIEF SUMMARY

According to an embodiment of the disclosure a prosthetic heart valve includes a collapsible and expandable stent extending from an inflow end to an outflow end, and a plurality of prosthetic valve leaflets coupled to the stent. Each leaflet may have a leaflet belly. The prosthetic heart valve may include a sealing ring coupled to the inflow end of the stent, the sealing ring comprising a tube extending circumferentially around the inflow end of the stent, wherein the tube is formed from a wire coiled into a repeating shape such that the tube is collapsible. The sealing ring may be axially offset from the leaflet belly when the stent is in a collapsed condition.

According to another embodiment of the disclosure, a prosthetic heart valve includes a collapsible and expandable stent extending from an inflow end to an outflow end and a plurality of prosthetic valve leaflets coupled to the stent. Each leaflet may have a leaflet belly. The prosthetic heart valve may include a sealing ring coupled to the inflow end of the stent, the sealing ring comprising a tube extending circumferentially around the inflow end of the stent, a covering at least partially surrounding the tube, and at least one of a first filler positioned within the tube and a second filler positioned between the tube and the covering. The sealing ring may be axially offset from the leaflet belly when the stent is in a collapsed condition.

According to a further embodiment of the disclosure, a prosthetic heart valve includes a collapsible and expandable stent extending from an inflow end to an outflow end and a plurality of prosthetic valve leaflets coupled to the stent. Each leaflet may have a leaflet belly. The prosthetic heart valve may also include a sealing ring coupled to the inflow end of the stent, the sealing ring comprising a tube extending circumferentially around the inflow end of the stent and a covering at least partially surrounding the tube, wherein the covering has a first end and a second end, the first end coupled to the stent by a first thread. The sealing ring may be axially offset from the leaflet belly when the stent is in a collapsed condition.

BRIEF DESCRIPTION OF THE DRAWINGS

Various embodiments of the presently disclosed prosthetic heart valve may be more fully understood with reference to the following detailed description when read with the accompanying drawings, in which.

DETAILED DESCRIPTION

As used herein, the term "inflow end," when used in connection with a prosthetic heart valve, refers to the end of the heart valve through which blood enters when the valve is functioning as intended. The term "outflow end," when used in connection with a prosthetic heart valve, refers to the end of the heart valve through which blood exits when the valve is functioning as intended. As used herein, the terms "generally," "substantially," and "about" are intended to mean that slight deviations from absolute are included within the scope of the term so modified. Like numbers refer to similar or identical elements throughout. When used herein in the context of a prosthetic heart valve, or a component thereof, the lengthwise or axial direction refers to a direction along a longitudinal axis passing through the center of the stent or heart valve. When used herein in the context of a prosthetic heart valve, or a component thereof, the circumferential direction refers to a direction extending along the circumference of the prosthetic heart valve.

Figure 1:
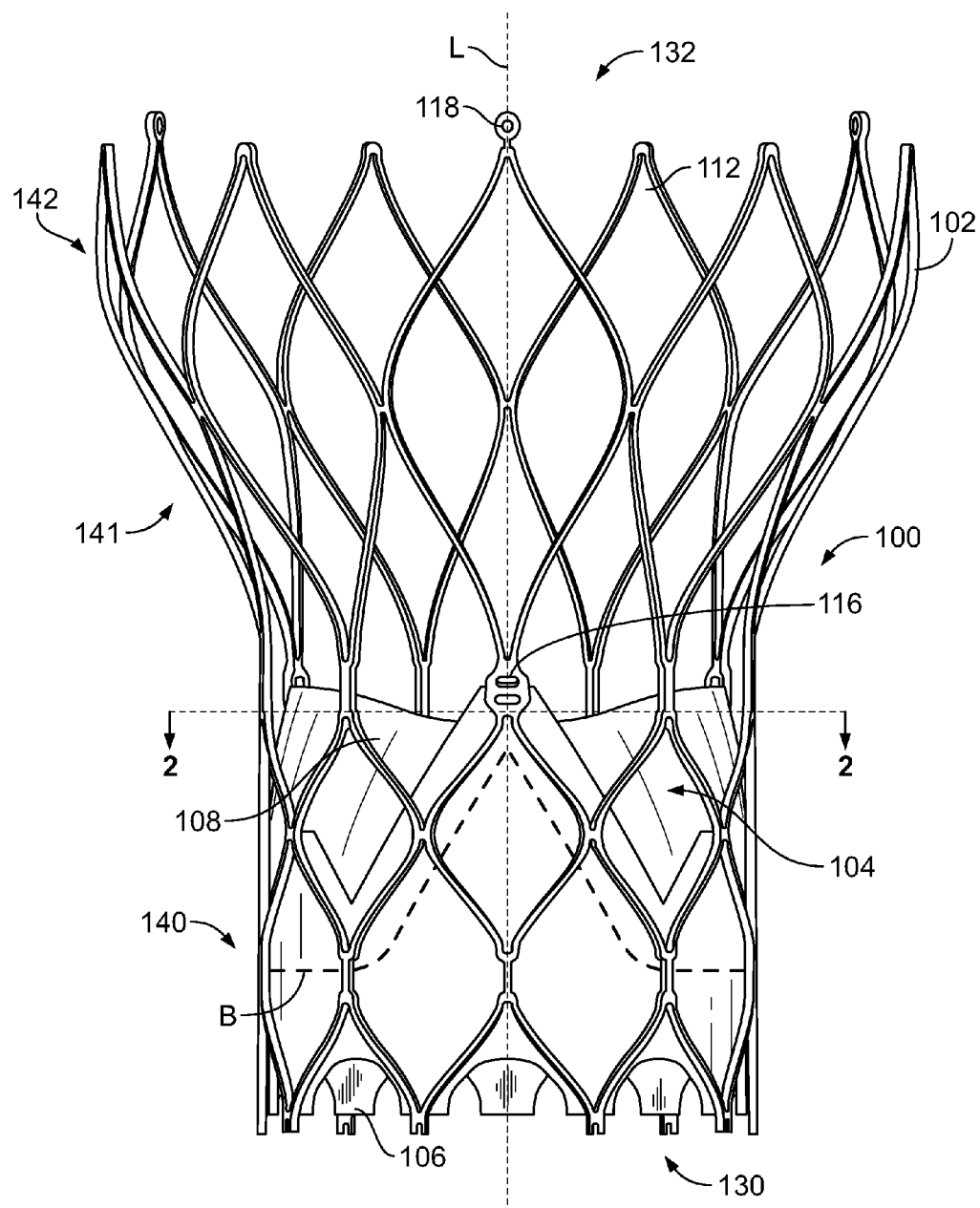
FIG. 1 is a front view of a collapsible prosthetic heart valve according to the prior art.

The sealing portions of the present disclosure may be used in connection with collapsible prosthetic heart valves. FIG. 1 shows one such collapsible stent-supported prosthetic heart valve 100 in an expanded condition. The prosthetic heart valve 100 is designed to replace the function of a native aortic valve of a patient. The prosthetic heart valve 100 includes a stent constructed as a frame 102. The stent 102 extends in a lengthwise or axial direction L from an inflow or annulus end 130 to an outflow or aortic end 132, and includes an annulus section 104 adjacent the inflow end 130 and an aortic section 142 adjacent the outflow end 132. The annulus section 104 has a relatively small cross section in the expanded condition, while the aortic section 142 has a relatively large cross section in the expanded condition. The annulus section 104 may be in the form of a cylinder having a substantially constant diameter along its length. A transition section 141 may taper outwardly from the annulus section 104 to the aortic section 142. Each of the sections of the stent 102 includes a plurality of cells 112 connected to one another in one or more annular rows around the stent 102. For example, as shown in FIG. 1, the annulus section 104 may have two annular rows of complete cells 112 and the aortic section 142 and the transition section 141 may each have one or more annular rows of complete or partial cells 112. The cells 112 in the aortic section 142 may be larger than the cells 112 in the annulus section 104. The larger cells 112 in the aortic section 142 may better enable the prosthetic valve 100 to be positioned without the stent structure 102 interfering with blood flow to the coronary arteries. At least partly due to the shape of cells 112, the stent 102 elongates in the lengthwise direction L as cells 112 collapse when the stent 102 is transitioned from the expanded condition to the collapsed condition.

The stent 102 may include one or more retaining elements 118 at the outflow end 132, the retaining elements 118 being sized and shaped to cooperate with retaining structures provided on a deployment device (not shown). The engagement of the retaining elements 118 with the retaining structures on the deployment device may help maintain the prosthetic heart valve 100 in assembled relationship with the deployment device, minimize longitudinal movement of the prosthetic heart valve relative to the deployment device during unsheathing or resheathing procedures, and help prevent rotation of the prosthetic heart valve relative to the deployment device as the deployment device is advanced to the target location and during deployment. One such deployment device is shown in U.S. Patent Publication No. 2012/0078352, the entire contents of which are hereby incorporated by reference herein.

The stent 102 may also include a plurality of commissure points 116 for mounting the commissures (not identified) of the valve assembly discussed below to the stent 102. As can be seen in FIG. 1, the commissure points 116 may lay at the intersection of four cells 112, two of the cells 112 being adjacent one another in the same annular row, and the other two cells 112 being in different annular rows and lying in end to end relationship. The commissure points 116 may be positioned entirely within the annulus section 104 or at the juncture of annulus section 104 and the transition section 141. The commissure points 116 may include one or more eyelets which facilitate the suturing of the leaflet commissure to the stent.

The prosthetic heart valve 100 includes a valve assembly 140 positioned in the annulus section 104. In the particular embodiment depicted, the valve assembly includes three leaflets 108. Two leaflets join one another at each of three commissures. When implanted at the native aortic valve annulus, blood flows from the inflow end 130, past leaflets 108, and toward the outflow end 132. This occurs when pressure in the left ventricle is greater than the pressure in the aorta, forcing the leaflets 108 to open. When pressure in the aorta is greater than pressure in the left ventricle, the leaflets 108 are forced closed and coapt with one another along free edges of the leaflet 108, blocking blood from flowing in a retrograde fashion from the outflow end 132 to the inflow end 130. The valve assembly 140 may be mounted to the stent 102 by suturing the commissures of the leaflets 108 to the commissure points 116 and suturing other portions of the valve assembly 140 to the stent 102, or by other methods known in the art. The valve assembly 140 may include a cuff 106 and a plurality of leaflets 108 which collectively function as a one way valve by coapting with one another. FIG. 1 illustrates a prosthetic heart valve for replacing a native tricuspid valve, such as the aortic valve. Accordingly, the prosthetic heart valve 100 is shown in FIG. 1 with three leaflets 108, as well as three commissure points 116. However, it will be appreciated that the prosthetic heart valves according to aspects of the disclosure may have a greater or lesser number of leaflets 108 and commissure points 116.

The leaflets 108 may define a leaflet belly B, indicated with broken lines in FIG. 1. The leaflet belly B is the portions of valve assembly 140 above which leaflets 108 are free to move radially inwardly to coapt with one another along their free edges. With this configuration, the valve assembly 140 is particularly thick at points at or above leaflet belly B. As such, any additional material axially aligned with valve assembly 140 above (or distal to) leaflet belly B may add significantly to the crimp profile of the valve 100.

Although the cuff 106 is shown in FIG. 1 as being disposed on the lumenal or inner surface of the annulus section 104, the cuff 106 may be disposed on the ablumenal or outer surface of annulus section 104, or may cover all or part of either or both of the lumenal and ablumenal surfaces of the annulus section 104. As is shown in FIG. 1, in one example the entirety of the valve assembly 140, including the leaflet commissures, is positioned in the annulus section 104 of the stent 102. When opened, the leaflets may extend further into the transition region 141 or may be designed such that they remain substantially completely within the annulus region 104. In this embodiment, substantially the entirety of the valve assembly 140 is positioned between the proximal end 130 of stent 102 and the commissure points 116, and none of the valve assembly is positioned between the commissure points 116 and the distal end 132 of the stent 102.

In operation, the embodiments of the prosthetic heart valve 100 described above may be used to replace a native heart valve, such as the aortic valve, a surgical heart valve, or a heart valve that has undergone a surgical procedure. The prosthetic heart valve 100 may be delivered to the desired site (e.g., near a native aortic annulus) using any suitable delivery device. During delivery, the prosthetic heart valve 100 is disposed inside the delivery device in the collapsed condition. The delivery device may be introduced into a patient using any known procedures, such as a transfemoral, transapical, or transseptal approach. Once the delivery device has reached the target site, the user may deploy the prosthetic heart valve 100. Upon deployment, the prosthetic heart valve 100 expands into secure engagement within the native aortic annulus. When the prosthetic heart valve 100 is properly positioned inside the heart, it works as a one-way valve, allowing blood to flow in one direction and preventing blood from flowing in the opposite direction.

Figure 2:
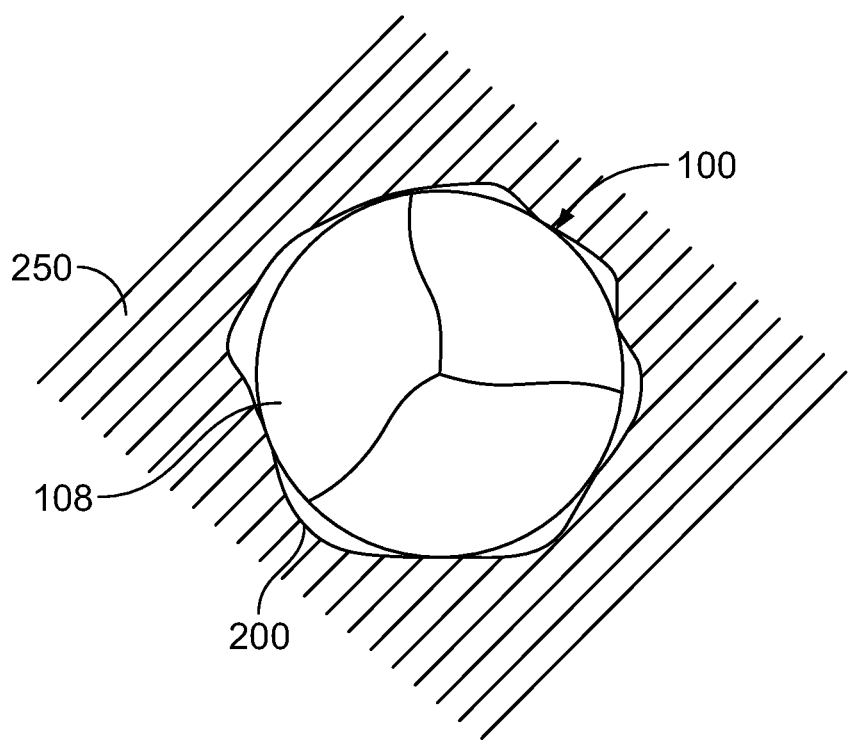
FIG. 2 is a top cross-sectional view of the prosthetic heart valve of FIG. 1 implanted in a patient taken along line 2-2.

FIG. 2 is a highly schematic cross-sectional illustration of the prosthetic heart valve 100 having leaflets 108 disposed within the native valve annulus 250, taken along line 2-2 shown in FIG. 1. As seen in FIG. 2, the substantially circular annulus section 104 of the stent 102 is disposed within a non-circular native valve annulus 250. At certain locations around the perimeter of the prosthetic heart valve 100, gaps 200 form between the heart valve 100 and the native valve annulus 250. Blood flowing through these gaps and around the valve assembly 140 of the prosthetic heart valve 100 can result in PV leak or regurgitation and other inefficiencies which can reduce cardiac performance. Such improper fitment may be due to suboptimal native valve annulus geometry due, for example, to calcification of the native valve annulus 250 or due to unresected native leaflets.

Figure 3A:
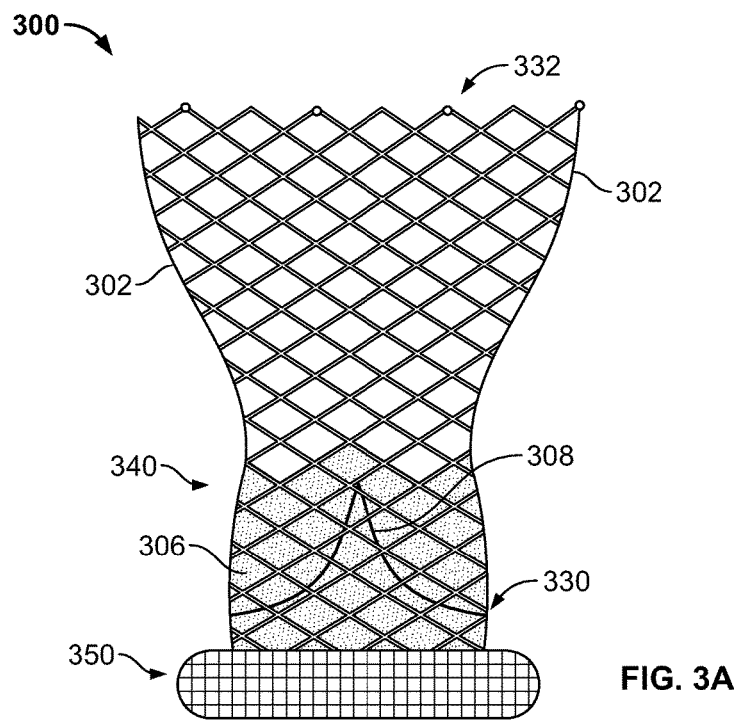
FIG. 3A is a highly schematic side view of one embodiment of a heart valve having a sealing ring intended to fill irregularities between the heart valve and the native valve annulus.

FIG. 3A illustrates a heart valve 300 according to one embodiment of the disclosure intended to reduce the likelihood and severity of PV leak between the heart valve and a native valve annulus. Heart valve 300 may have a stent 302 which extends between inflow end 330 and outflow end 332, a valve assembly 340 having a plurality of leaflets 308, and a cuff 306. Heart valve 300 may be formed of any of the materials and in any of the configurations described above with reference to FIG. 1.

The stent 302 may be wholly or partly formed of any biocompatible material, such as metals, synthetic polymers, or biopolymers capable of functioning as a stent. Suitable biopolymers include, but are not limited to, elastin, and mixtures or composites thereof. Suitable metals include, but are not limited to, titanium, nickel, stainless steel, and alloys thereof, including nitinol. Other metals that have elastic and/or memory properties may also be suitable, such as spring stainless steel, trade named alloys such as Elgiloy®, and Hastelloy®, CoCrNi alloys (e.g., trade name Phynox), MP35N®, CoCrMo alloys, mixtures of such alloys or mixtures of metal and polymer fibers. Suitable synthetic polymers for use as a stent include, but are not limited to, thermoplastics, such as polyolefins, polyesters, polyamides, polysulfones, acrylics, polyacrylonitriles, polyetheretherketone (PEEK), and polyaramides. Furthermore, the stent 302 need not be cylindrically shaped. For example, stent 302 may take the shape of an ellipse or other shapes, such as a general "D" shape with a substantially straight section and an arcuate section extending from one end of the straight section to the other. Such a "D" shape may better conform to particular anatomies, such as the mitral valve, the tricuspid valve, or a diseased bicuspid valve. Other portions of the valve, such as the sealing ring 350, described in greater detail below, may take similar shapes, for example depending on the stent 302 on which they are positioned.

The valve assembly 340 may be wholly or partly formed of any suitable biological material or polymer. Examples of biological materials suitable for the valve assembly 340 include, but are not limited to, porcine or bovine pericardial tissue. Examples of polymers suitable for the valve assembly 340 include, but are not limited to, polyurethane, silicone, PTFE, and polyester. In at least some examples, portions of valve assembly 340, a cuff and the suture used may include an ultra-high molecular weight polyethylene. An example of one such valve assembly 340 is disclosed in U.S. Patent Publication No. 2010/0185277, the entire contents of which are hereby incorporated by reference herein. Although valve assembly 340 typically includes one or more leaflets, other suitable valve assemblies without leaflets that work as one-way valves may be alternately used.

Similar to cuff 106, cuff 306 may be disposed on the lumenal side of stent 302, the ablumenal side of stent 302, or both. Both the cuff 306 and the leaflets 308 may be wholly or partly formed of any suitable biological material or polymer, including those, such as PTFE, described above in connection with the prosthetic heart valve 300. Additionally, the cuff 306 may be formed from polyurethane copolymers or include ultra-high molecular weight polyethylene.

It should be noted that while the disclosure herein is predominately discussed in terms of a tricuspid valve, i.e., a valve having three distinct mutually coapting leaflets, and a stent having a shape as illustrated in FIG. 3A, the valve and stent may take other forms. For example, the valve could be a bicuspid valve, i.e., a valve having two coapting leaflets, or other types of valves, including valves with greater or fewer leaflets as well as non-leaflet valves. Similarly, the stent could have different shapes, such as a flared or conical annulus section, a more or less bulbous aortic section, a differently shaped transition section between the aortic section and the annulus section, any other suitable shape, and may or may not be collapsible.

Figure 3B:
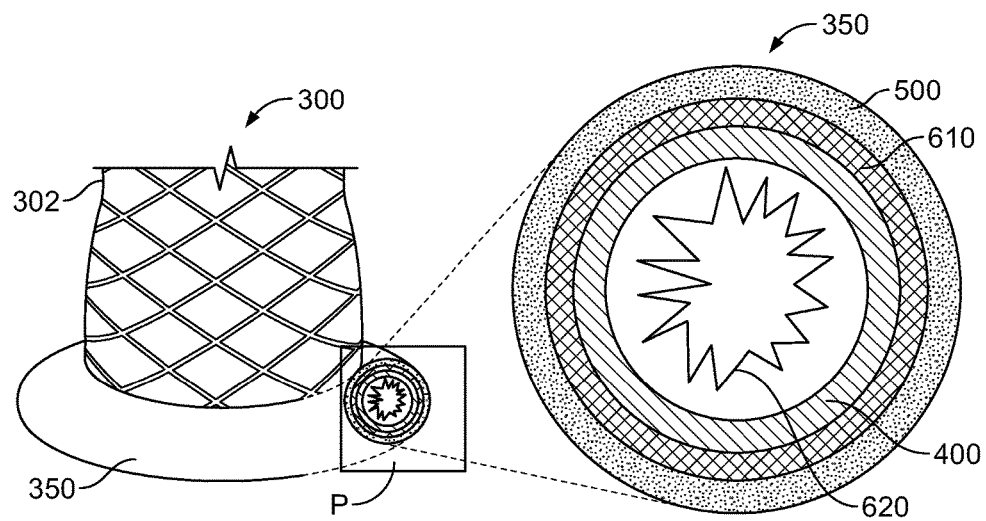
FIG. 3B is a highly schematic cross-sectional view of the sealing ring of FIG. 3A.

Heart valve 300 may include a sealing element, such as sealing ring 350, at or near inflow end 330 of stent 302 to help mitigate PV leak, as illustrated in FIG. 3A. FIG. 3B illustrates an enlarged cross-sectional view of sealing ring 350 taken along a cutting plane P transverse to the circumferential direction of sealing ring 350. Generally, sealing ring 350 may comprise tube 400 with or without a covering 500, with optional outer filler 610 between the covering 500 and the tube 400, and with optional inner filler 620 inside the tube 400. Unless stated otherwise, the term filler, as used herein, refers to the outer filler 610 and/or the inner filler 620. Sealing ring 350 may include any combination of tube 400, covering 500, and filler. If outer filler 610 is used, covering 500 may be required to contain outer filler 610 within sealing ring 350. Prior to describing sealing ring 350 in greater detail, the function of sealing ring 350 is briefly explained.

Figure 3C:
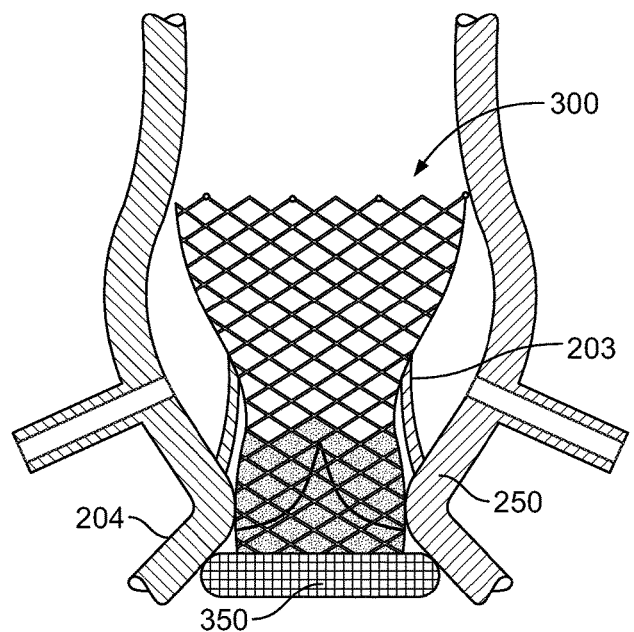
FIG. 3C is a highly schematic side view of the heart valve of FIG. 3A implanted into a native valve annulus with unresected native valve leaflets.
Figure 3D:
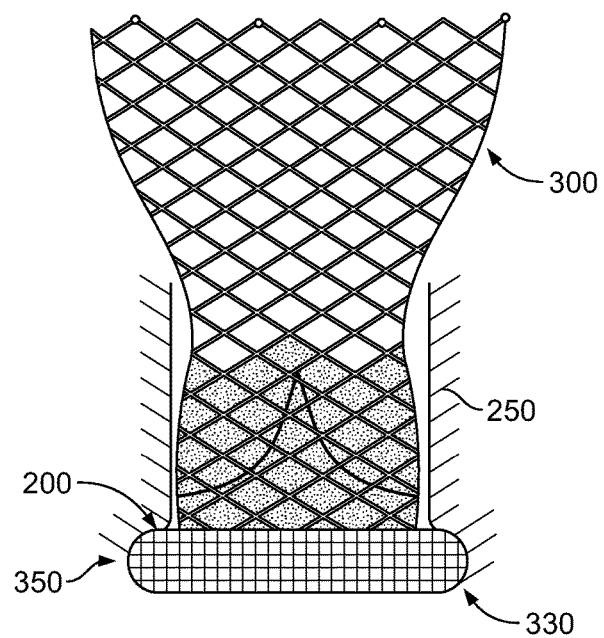
FIG. 3D is a highly schematic side view of the heart valve of FIG. 3A implanted into a native valve annulus with resected native valve leaflets.

FIGS. 3C-D illustrate heart valve 300 disposed within a native valve annulus 250 adjacent unresected native leaflets 203 and adjacent resected leaflets, respectively. When implanted within native valve annulus 250, sealing ring 350 may be disposed, for example, below the native valve annulus 250 (i.e., in a sub-annular position) or below native leaflets 203 (i.e., in a sub-leaflet position). As shown in FIG. 3C, sealing ring 350 is disposed such that it is in contact with the left ventricular outflow tract ("LVOT") 204, although it may be disposed within the native annulus 250, or at the juncture between native annulus 250 and LVOT 204. Such positioning helps to provide a seal between heart valve 300 and the native heart tissue. For example, as illustrated in FIG. 3D, despite gaps 200 between heart valve 300 and native valve annulus 250, sealing ring 350 helps prevent retrograde blood flow around the outer circumference of valve 300. Sealing ring 350 may additionally help prevent heart valve 300 from migrating into the aorta when implanted at the native aortic valve annulus. It should be noted that the sealing ring 350 may be flexible such that it conforms to the geometry in which it is positioned. For example, sealing ring 350 may conform to the LVOT 204, native annulus 250, or any other structure to a greater degree than illustrated in FIG. 3C. Also, as should be understood, sealing ring 350 may be positioned below the native annulus 250, at the native annulus 250, above the native annulus 250, or any combination thereof, for example being in contact with the native annulus 250 and extending slightly below the native annulus 250 as well.

As noted above, sealing ring 350 may include elements such as tube 400, covering 500, and filler material. Generally, tube 400 may provide a structural support onto which covering 500 may be attached and into which outer filler 610 or inner filler 620 may be inserted. Tube 400 alone may provide sealing of prosthetic valve 300, although such sealing may be enhanced with the addition of covering 500 and/or filler.

While the intent of sealing ring 350 is to mitigate and/or prevent PV leak, there is generally a correlation between the amount of material forming valve 300 and the size of the valve when crimped to a collapsed condition. When using a collapsible and expandable prosthetic valve, such as valve 300, the valve 300 is generally crimped into a collapsed condition for loading within a sheath of a delivery device that is delivered through the body, such as through the vasculature, to the site of implantation. As such, a large crimp profile for valve 300 generally requires the delivery device to incorporate a correspondingly large diameter sheath. As used herein, the term "crimp profile" generally refers to the largest diameter of a prosthetic valve when it is in a collapsed condition. A large diameter delivery system may be incapable of being passed through the patient's vasculature, while a delivery system having a smaller diameter and housing a heart valve with a smaller crimp profile may be easier to navigate through the patient's body and may also reduce the operation time.

As illustrated in FIGS. 3A, 3C, and 3D, sealing ring 350 may be attached to inflow end 330 of valve 300. In particular, sealing ring 350 may be positioned such that it does not overlap in the axial direction, or only minimally overlaps, the region of the valve having prosthetic leaflets 308 when the prosthetic heart valve 300 is in the collapsed condition. In particular, the sealing ring 350 may be axially offset from the belly regions of the prosthetic leaflets 308. There may also be little or no axial overlap when the prosthetic heart valve 300 is in the expanded condition, as shown in FIGS. 3A, 3C and 3D. As used herein, "axial overlap" refers to portions of two structures being within the same radial line extending perpendicularly from the lengthwise direction L. With this configuration, when prosthetic valve 300 is crimped into a collapsed condition, such as for loading onto a delivery device, there is little or no axial overlap between sealing ring 350 and the region of valve 300 at which prosthetic leaflets 308 are positioned. As a result, valve 300 may have a smaller crimp profile compared to another prosthetic valve having the same sealing ring located closer toward the region at which prosthetic leaflets 308 are positioned.

In one example, sealing ring 350 is positioned such that approximately half of the sealing ring is positioned above (i.e. circumferentially overlapping) the stent 302 at its inflow end 330 and approximately half of the sealing ring is positioned below (i.e. not circumferentially overlapping) the stent at its inflow end when valve 300 is in the expanded condition. In another example, sealing ring 350 may be nearly completely positioned below the stent 302 at its inflow end 330 when valve 300 is in the expanded condition. In a further example, the proximalmost end of the sealing ring 350 may substantially align with the proximal most portion of the inflow end 330 of the stent 302 when valve 300 is in the expanded condition. When used herein in the context of a prosthetic heart valve, the term proximal refers to a direction closer to the inflow end of the valve, while the term distal refers to a direction closer to the outflow end of the valve.

In addition to the positioning of sealing ring 350 with respect to other components of valve 300, the material and structure of the components of sealing ring 350 may have an effect on the effectiveness of mitigating PV leak while maintaining a relatively small crimp profile.

Tube 400 of sealing ring 350 may be formed of various materials. In addition, the material forming tube 400 may have one or more of a variety of structures. For example, the material of tube 400 may be individual strands braided into a generally tubular mesh structure, or may be an individual strand formed into a coil. For a braided tube 400, the strands forming the braid may have a particular relative orientation with respect to one another (e.g., a helical braid).

Covering 500 may be formed of one or more materials having low permeability or no permeability to water and/or blood. For example, covering 500 may be formed of tissue, including but not limited to pericardium or other sheet-like tissue obtained from animals or by tissue engineering. The covering 500 may be formed of a fabric-type material, such as a fabric formed of polytetrafluoroethylene (PTFE), polyethylene terephthalate (PET), or ultra-high molecular weight polyethylene (UHMWPE). The covering 500 may also be formed of synthetic or natural polymers, such as silicones, polyvinyl alcohol (PVA), or collagen sheets. The covering 500 may be formed of any one or any combination of the above-listed materials.

The filler may be formed of any of a variety of materials. For example, the filler may be composed of the same material described in connection with tube 400, such as a coil or mesh braid formed of Nitinol. The filler may also be composed of any material described in connection with covering 500, such as fabrics, tissues, and synthetic or natural polymers. Furthermore, the filler may be composed of a water swellable material, such natural sea sponge or beads, or other materials that expand upon exposure to body conditions. This may include, for example, PVA microspheres that expand upon contact with blood. Other materials that expand after exposure to temperatures found in the body or components of the blood may also be suitable for the filler. Another potential material for filler is a highly compressible sponge, for example one made from alginate cross-linked at low temperatures. Such a highly compressible sponge may collapse to a large extent when shear forces are applied, while being able to return to an original shape upon removal of the forces. Such a property may contribute to a smaller valve crimp profile while retaining the ability to "spring back" to an original shape upon deployment of the valve. Further, a single filler composed of a single material or a combination of materials described above may be used, or multiple fillers each composed of one or a combination of any of the above materials may be used.

In one embodiment, prosthetic valve 300 may include sealing ring 350 that includes tube 400 formed of braided mesh of a shape-memory material, of a super-elastic material, of a bio-compatible polymer, or of another material that is capable of being collapsed and expanded into a desired shapes. Generally, tube 400 takes the shape of a hollow annulus wrapped around a portion of stent 302, such that tube 400 generally forms a hollow torus. It should be understood that tube 400 need not meet the precise mathematical definition of a torus or other toroid. Tube 400 may comprise a braided metal fabric that is both resilient and capable of heat treatment to substantially set a desired shape, such as Nitinol, or any other metal suitable for use of stent 302 described above. However, it should be understood that other materials, such as braided polymers, including polypropylene, may be used for the braided mesh version of tube 400. Depending on the individual material selected, the strand diameter, number of strands, and pitch may be altered to achieve the desired properties for tube 400. If sealing ring 400 comprises only braided mesh, the braided tube 400 may help in reducing PV leak, for example by creating a seal as blood clots form in the braid. PV leak may be further mitigated to the extent tissue in-growth occurs on the sealing ring 350, such as by endothelialization and/or epithelialization. Such sealing by clotting and/or thrombus formation may take up to an hour or more to form, with tissue in-growth occurring over a longer time. However, faster sealing may be a desirable result. For example, faster sealing may provide a physician with immediate or near immediate feedback that PV leak is not occurring at unacceptable levels, regardless of the fact that PV leak may be appropriately mitigated given the amount of time required for clotting in the braided tube 400. As is described in greater detail below, a covering 500 and/or filler may be used in combination with a braided tube 400 (or a coiled tube 400 as described below) to accelerate sealing and enhance tissue in-growth.

One of the advantages of using braided Nitinol for tube 400 is that the structure relatively easily undergoes a transition into different shapes. For example, it may be easily collapsible for delivery, easily expandable upon implantation, and may change shape as appropriate to fill in gaps 200 in native annulus 250. However, as noted above, it may be desirable to add a covering 500 and/or filler if tube 400 is formed of braided mesh. The addition of such material may change the way the braided mesh changes shapes. For example, if the braid is covered tightly with a covering 500, the braid may not behave the same as it would without such a covering. One possible solution to this challenge is the choice of material for covering 500 and/or filler material, as well as the way the covering 500 is attached to tube 400, which is described in greater detail below. Another possible solution is to use a different structure for tube 400.

Instead of forming tube 400 of a braided mesh, it may be desirable to form tube 400 from a coiled material, such as coiled Nitinol (or any other material suitable for use in forming stent 302). In particular, tube 400 may be formed of a single strand of material, or single stands of material attached end-to-end, coiled into a desired shape. For example, tube 400 may be formed of a strand of Nitinol coiled into a circular shape, a rectangular shape, or a diamond shape. The strand of material forming the coil may have various cross-sectional shapes, such as round, flat (e.g. a ribbon), or rectangular. Still further, the coiled wire may take the form of a coil, multiple wires wound together in different directions (e.g., a braid), two or more wires wound together in the same direction (e.g., two wires wound as a double helix). The coiled wire may be later cut from a tube and may have varying diameters along the length of the coil. In addition, the coil need not be a closed coil, but may be an open coil having, for example, a "U" or "C" shape.

Generally, tube 400 may have different qualities when formed from a coil compared to a braided mesh. For example, a tube 400 formed from a coil may collapse to a smaller profile than a similar tube formed of a braided mesh. On the other hand, if sealing ring 350 is formed solely of tube 400 comprising a coil, sealing via clotting may be slower or may never occur at all compared to the braided mesh version. But when a covering 500 and/or filler is included with a tube 400 formed of a coil, the sealing ring 350 may seal against PV leak rapidly. However, it should be clear that a covering 500 and/or filler may similarly be used in conjunction with a braided mesh version of tube 400.

Figure 4B:
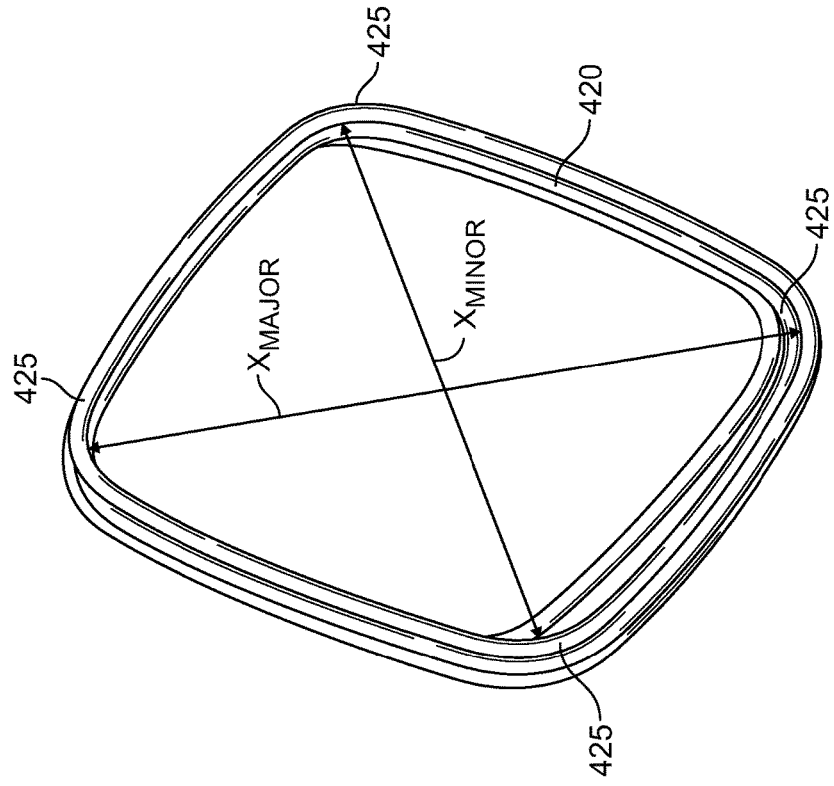
FIG. 4B is a front view of a diamond coil of a sealing ring.
Figure 4A:
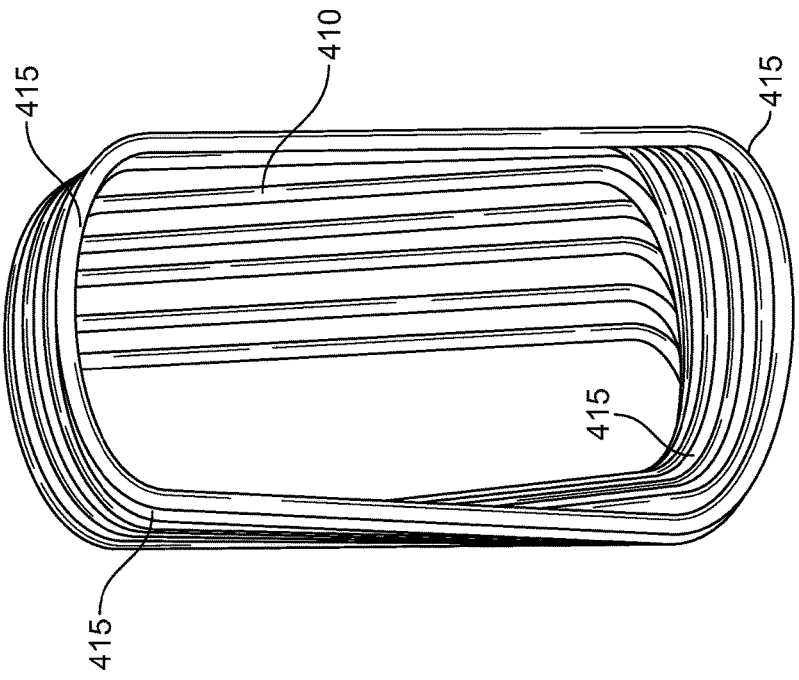
FIG. 4A is a front view of a rectangular coil of a sealing ring.

As noted above, when tube 400 is formed of a coil, the coil may take different general shapes, such as that of a circle (not illustrated), of a rectangle (FIG. 4A), or a diamond (FIG. 4B). The coils shown in FIG. 4A-B are viewed along the same cutting plane P shown in FIG. 3B. As such, multiple turns or iterations of each coil shape are visible in FIGS. 4A-B. Stated more precisely, the shape of the coil is a rectangle (FIG. 4A) or a diamond (FIG. 4B) when an individual turn of the coiled wire is projected onto a plane. The use of a rectangular coil 410 or diamond coil 420 for tube 400 may have an advantage in that the respective coils are more readily collapsible than, for example, a circular coil or braided mesh. In particular, the corners 415 of rectangular coil 410 and the peaks 425 of diamond coil 420 facilitate the respective coils collapsing during loading, delivery, and/or resheathing of valve 400. Benefits of the tube 400 being readily collapsible may include a reduced overall delivery profile, as well the requirement of relatively little force to load and/or resheath prosthetic valve 300 prior to being fully released in the native annulus 250. It should be noted that rectangular coil 410 is shown in FIG. 4A (and diamond coil 420 in FIG. 4B) not in the form of tube 400, but rather a segment thereof. In stent 300, rectangular coil 410 or diamond coil 420 would extend along a circumferential path around inflow end 330 of valve 300, forming tube 400. As should be clear from the above, the term "tube" does not solely refer to an elongated cylindrical structure, as the rectangular coil 410 and diamond coil 420 extended circumferentially around stent 300 is still considered herein as a tube 400. In fact, although shown throughout this disclosure as a torus, the tube 400 need not be a toroid at all. For example, tube 400 of sealing ring may undulate such that points on the proximal (or distal) surface do not lie in the same plane as other points on the proximal (or distal) surface. As such sealing ring 350 may have an undulating quality as well.

Varying the geometry of the shape of the coil may provide for different effects in terms of profile and sealing. For example, when using a diamond coil 420, the lengths of the major axis $X_{MAJOR}$ and minor axis $X_{MINOR}$ may be, respectively, approximately 3 mm by approximately 2 mm, approximately 4 mm by approximately 2 mm, or approximately 4 mm by approximately 3 mm. The lengths of the major and minor axes should be understood to be examples, and not requirements. The examples given above may be useful for achieving a bulge in the sealing ring 350 of approximately 2-3 mm from the outer circumference of the stent 302, which may be particularly effective at reducing PV leak. Further, as noted above, wires having cross-sections other than circular, including flat and/or rectangular, may be used to form coil tube 400. Generally, the goal is to decrease the collapsed profile of the valve 300 including sealing ring 350, while retaining enough strength within the sealing ring 350 to push or abut against the native valve annulus 250 to eliminate or reduce any gaps 200 between the native valve annulus 250 and the prosthetic valve 300. While the thickness of the coil forming tube 400 may vary in size, particularly depending upon the shape of the coil, one exemplary range of thicknesses is between approximately 0.05 mm and approximately 0.175 mm. The term thickness in the context of a coiled wire refers to a cross-sectional dimension of the wire. For example, a coil having a circular cross-section has a thickness equal to the diameter of the cross-section. It should be noted that the above dimensions provided in relation to components of tube 400, as well as any other dimensions provided herein, are for illustrative purposes. Varying dimensions may be used without departing from the scope of this disclosure.

Other features of the braids and/or coiled wires forming tube 400 may be modified and optimized to achieve a better seal against PV leak, including, for example, the wire or braid density, shape, and stiffness. Also, when tube 400 is formed of a coiled wire, the ratio of thickness of the coil to the spacing between adjacent iterative shapes of the coil (i.e., pitch) may have an effect on PV leak sealing. For example, a relatively large pitch may lead to kinking or tenting (i.e., a deviation from a smooth circumference) in the tube 400, which may reduce the effectiveness of sealing against PV leak. In some embodiments, it may be preferable that the ratio of coil thickness to the pitch is between approximately 1:6 and approximately 1:32.

As noted above, when tube 400 is formed of a coiled material, rather than a braided mesh, it may be advantageous to include a covering 500 that at least partially surrounds tube 400. It may also be advantageous to include a filler material inside and/or outside the tube 400. However, it should be understood that a covering 500 and filler may be used regardless of whether tube 400 is formed of a coil or a braided mesh. For example, if tube 400 is formed of either a metallic coil or a metallic braided mesh, a covering 500 may be desired to reduce the likelihood and/or severity of abrasion from metal-on-metal contact between tube 400 and stent 302.

FIGS. 5A-F are highly schematic cross-sectional drawings of an inflow portion 330 of valve 300 with a sealing ring 350 taken along the same cutting plane P illustrated in FIG. 3B. In these embodiments, sealing ring 350 comprises tube 400 and covering 500. In particular, tube 400 may take any form described above, such as a braided mesh or coil. The addition of covering 500 to tube 400, in particular a covering 500 with low or no permeability to water and/or blood, may facilitate creating a better seal between sealing ring 350 and the native valve annulus 250. In addition to physically blocking blood from flowing past the sealing ring 350, covering 500 may accelerate clotting within sealing ring 350 to the extent clotting occurs, and may further facilitate tissue ingrowth to create a better seal over time. Although some materials may have greater porosity than others, and thus greater permeability to water, those materials may be advantageous if, for example, they have relatively small thickness, relatively good tissue ingrowth, or other properties that help reduce the crimp profile of sealing ring 350 with valve 300.

Each embodiment of sealing ring 350 shown in FIGS. 5A-5F includes tube 400, covering 500, and one or more connections 510 connecting covering 500 to tube 400 and/or the stent 302 of valve 300. It should be noted that although connections 510 are described as being connected to the stent 302, connections may alternatively be connected to other portions of the prosthetic heart valve 300, such as the cuff 306, in addition or alternatively to the stent 302. Connections may be, for example, sutures or other strand-like material. Various stitch patterns, such as running stitches and whip stitches, may be used for connections 510. It should further be noted that, although tube 400 is generally described as being connected to valve 300 with stitching and/or sutures, other methods of connection, including welding, adhesives, etc. may be suitable in addition or in the alternative to stitching.

Figure 5A:
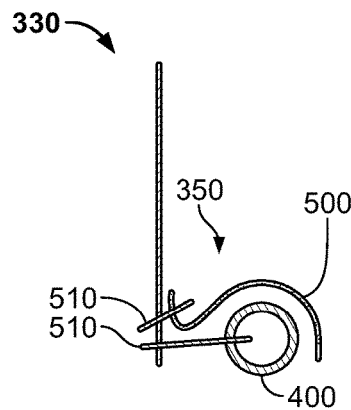
FIGS. 5A-5F are highly schematic cross sectional views of a portion of a prosthetic heart valve with a sealing ring comprising a tube and a covering.
Figure 5B:
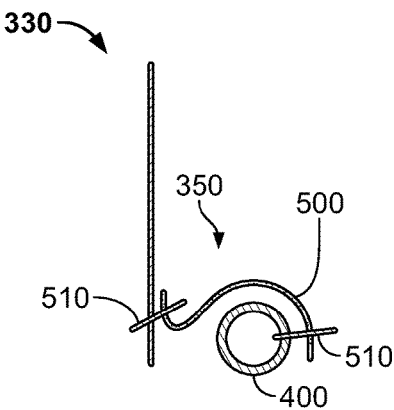
Figure 5C:
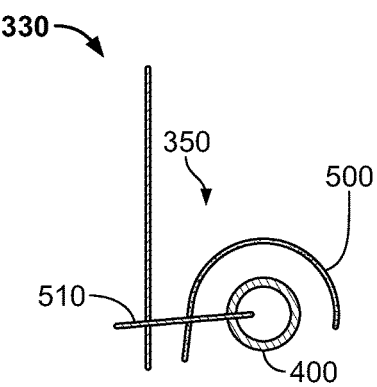
Figure 5D:
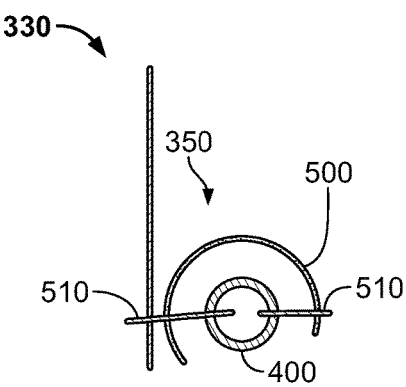
Figure 5E:
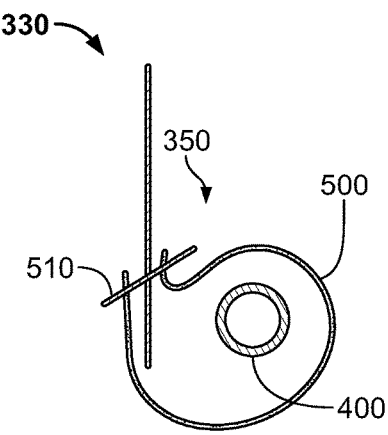
Figure 5F:
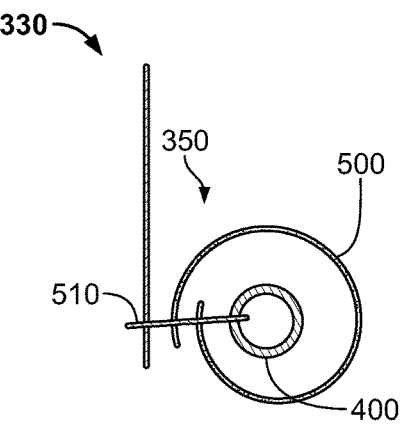

In FIG. 5A, one edge of covering 500 is stitched to stent 302, tube 400 is stitched to stent 302, and covering 500 does not surround the entire cross-section of tube 400. In FIG. 5B, one stitch 510 connects a first edge of covering 500 to stent 302, another stitch 510 connects the other edge of covering 500 to tube 400, and covering 500 does not surround the entire cross-section of tube 400. In FIG. 5C, one edge of covering 500 is connected to both stent 302 and tube 400 by a single stitch 510, and the covering 500 does not surround the entire cross-section of tube 400. In FIG. 5D, one edge of covering 500 is connected to both stent 302 and tube 400 with a first stitch 510, the other edge of covering 500 is connected to tube 400 with a second stitch 510, and the covering 500 does not cover the entire cross-section of tube 400. In FIG. 5E, covering 500 surrounds the entire cross-section of tube 400, and one stitch 510 connects each edge of covering 500 to stent 302. In FIG. 5F, covering 500 surrounds the entire cross-section of tube 400 and one stitch 510 connects each edge of covering 500 to both stent 302 and tube 400.

In each of the embodiments described in connection with FIGS. 5A-F, a number of stitches 510 may be used to connect covering 500 to tube 400 and/or stent 302 along the circumference of the inflow end 330 of the stent 302. It should be noted that there may be a benefit of using few or no sutures attaching covering 500 directly to tube 400. For example, particularly when tube 400 comprises braided Nitinol, tight and/or frequent stitches 510 connecting covering 500 directly to tube 400 may reduce the ability of tube 400 to predictably undergo a transition in shape to fill gaps 200 in native valve annulus 250. Additionally, allowing little or no slack between tube 400 and covering 500 may restrict the ability of tube 400 to change shape appropriately to fill in any gaps 200 between native valve annulus 250 and prosthetic valve 300. For example, the configurations illustrated in FIGS. 5A-D leave a proximal end of tube 400 exposed. If tube 400 is comprised of a wire coiled in a diamond shape 425, during expansion (or during collapsing), the diamond shape may grow in a lengthwise dimension as the peaks 425 of the minor axis $X_{MINOR}$ come together and the peaks 425 of the major axis $X_{MAJOR}$ move apart. The exposed proximal end of tube 400 may facilitate such change in shape. It should further be noted that, particularly in embodiments in which both edges of covering 500 are connected to the stent 302 and/or tube 400, the position of the covering 500 with respect to the tube 400 may be reversed. Taking the embodiment illustrated in FIG. 5D as an example, the covering 500 may be positioned to surround the proximal end of tube 400 leaving the distal end of tube 400 exposed. If the covering 500 takes this reverse position, it may be desirable to connect the covering to the valve 300 in a way to reduce the possibility of the covering 500 sliding with respect to the connection point, for example because of the force of gravity. Such connection may be made, for example, by attaching the covering 500 to an eyelet, groove, or other structure on stent 302, where the possibility of such sliding motion is limited. This reverse orientation may be applicable to remaining embodiments described below.

As should be clear from the above description, covering 500 need not surround the entire cross-section of tube 400, and may cover only the portion facing the direction of retrograde blood flow when implanted in an intended position. As illustrated in FIGS. 5A-F, this surface of tube 400 is oriented on the proximal end of tube 400, facing away from inflow end 330. Using a partial covering 500 may reduce the amount of material, and thus reduce the bulk and profile of valve 300 when in the collapsed condition, while covering 500 still is in contact with any retrograde blood flow contacting sealing ring 350. Covering 500 may still contact any retrograde blood flow contacting sealing ring 350 if oriented on the distal end of tube 400. Similarly, the greater the number of stitches 510 used, both in terms of the points of connection of covering 500 to tube 400 and stent 302, as well as the frequency of those stitches along the length of the circumference of stent 302, may effect the crimp profile of valve 300. Generally, as more stitches 510 are used, the crimp profile of valve 300 increases and the covering 500 is more tightly attached to tube 400. Although not described above, other combinations of stitch locations and configurations of covering 500 with respect to tube 400 and stent 302 may be suitable.

Figure 6A:
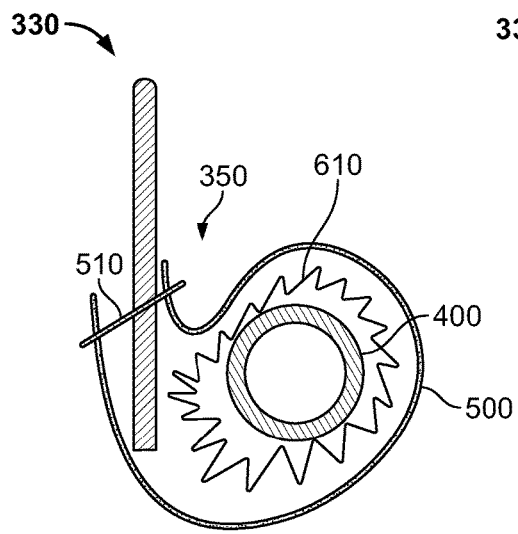
FIGS. 6A-D are highly schematic cross sectional views of a portion of a prosthetic heart valve with a sealing ring comprising a tube, a covering, and an outer filler.
Figure 6B:
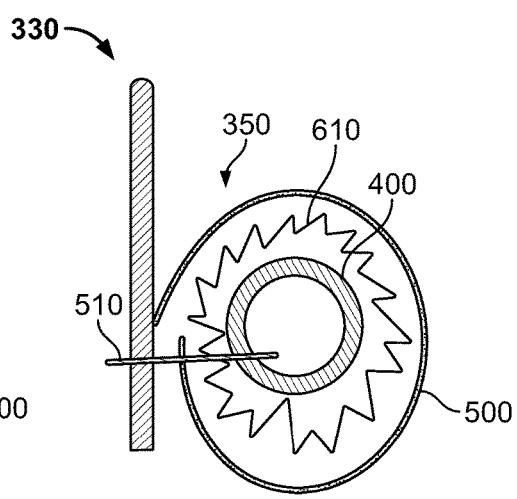
Figure 6C:
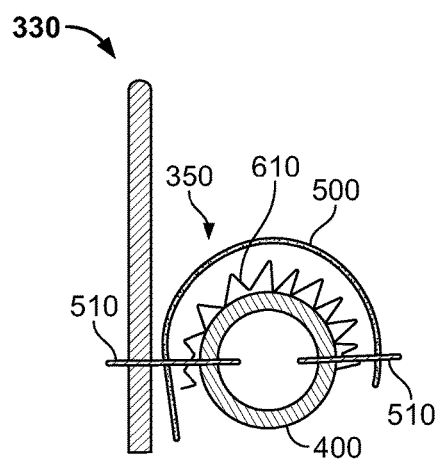
Figure 6D:
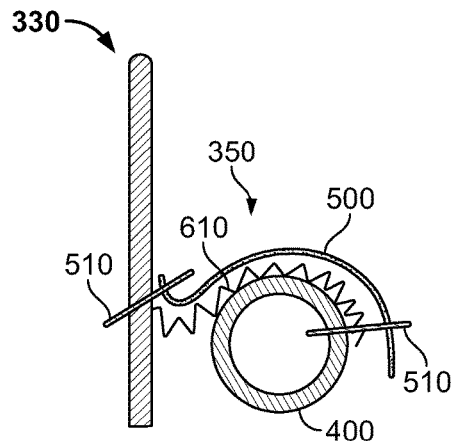
Figure 6E:
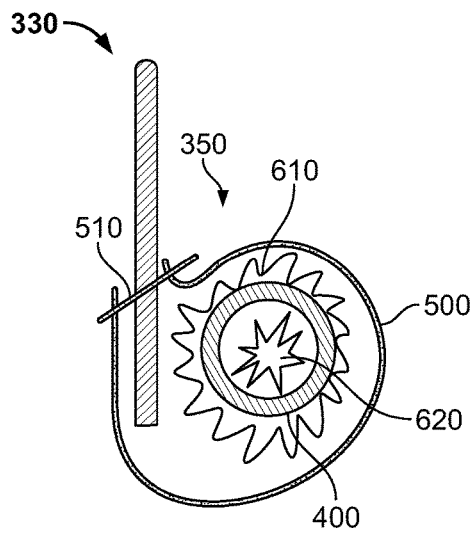
FIGS. 6E-H are highly schematic cross sectional views of a portion of a prosthetic heart valve with a sealing ring comprising a tube, a covering, an outer filler, and an inner filler.
Figure 6F:
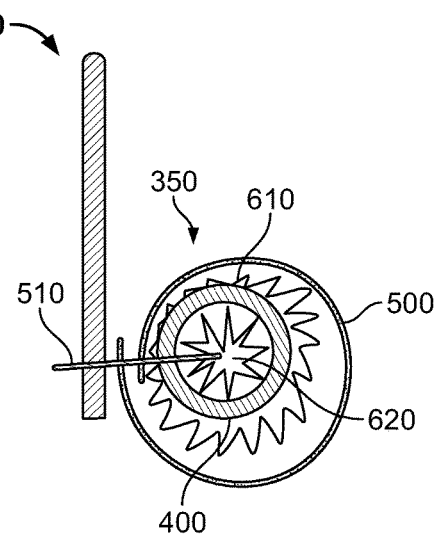
Figure 6G:
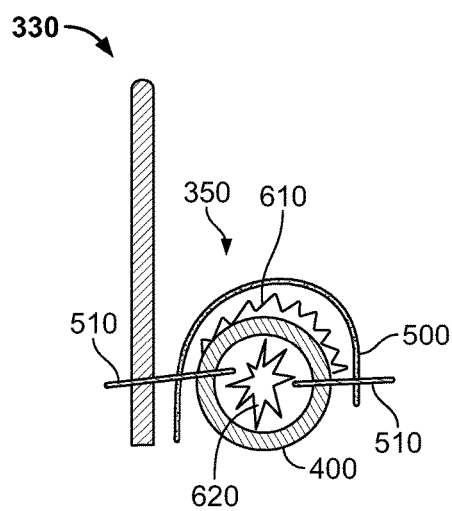
Figure 6H:
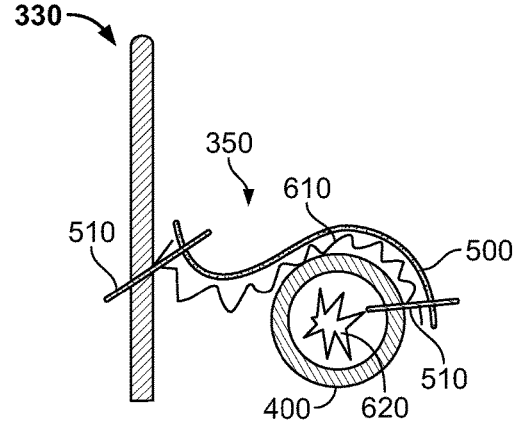
Figure 6I:
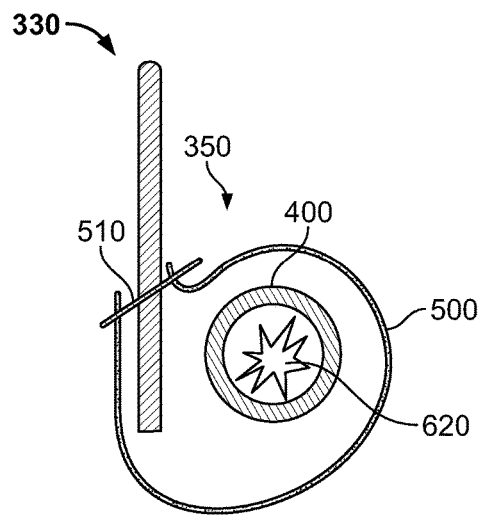
FIGS. 6I-N are highly schematic cross sectional views of a portion of a prosthetic heart valve with a sealing ring comprising a tube, a covering, and an inner filler.
Figure 6J:
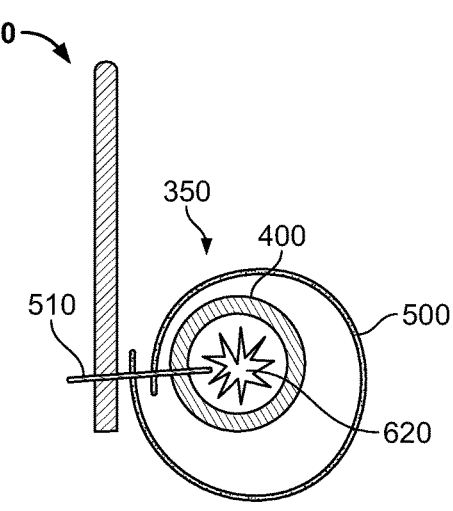
Figure 6K:
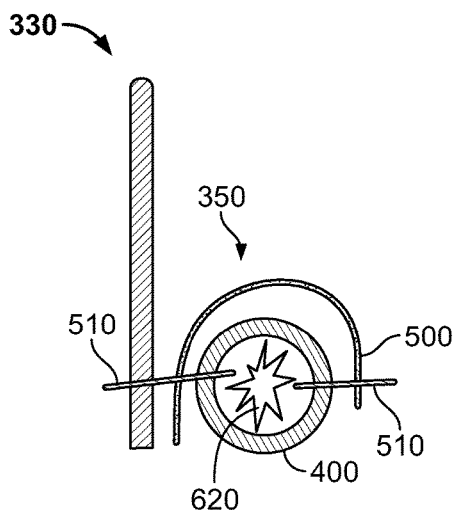
Figure 6L:
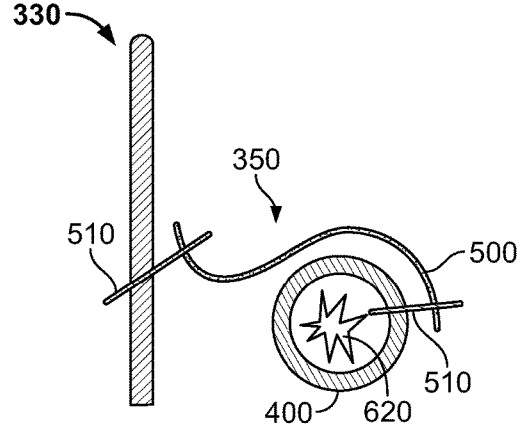
Figure 6M:
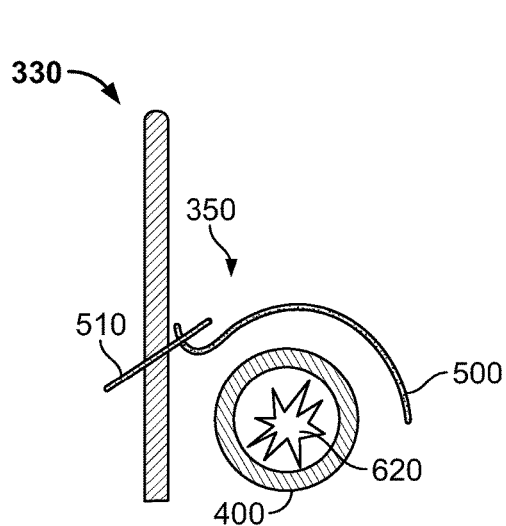
Figure 6N:
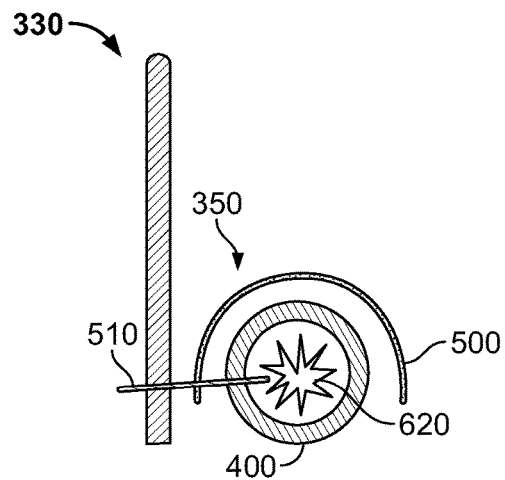
Figure 6O:
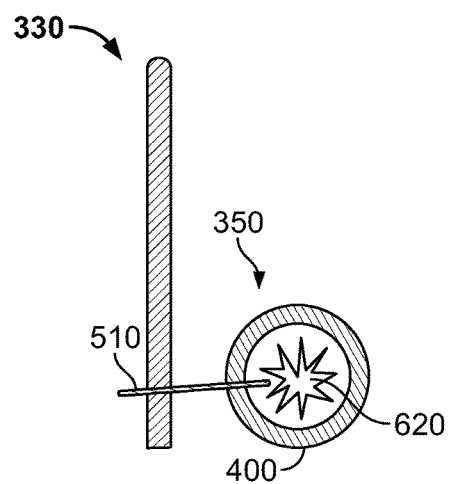
FIG. 6O is a highly schematic cross sectional view of a portion of a prosthetic heart valve with a sealing ring comprising a tube and an inner filler.

FIGS. 6A-O are highly schematic cross-sectional drawings of an inflow portion 330 of valve 300 with a sealing ring 350 taken along the same cutting plane P as shown in FIG. 3B. In these embodiments, sealing ring 350 comprises tube 400 and filler, with some embodiments also including covering 500. In particular, tube 400 may take any form described above, such as a braided mesh or coil. Covering 500, if used, may take any suitable form, such as those described above. The filler may be positioned completely or substantially within tube 400 (inner filler 620), between tube 400 and covering 500 (outer filler 610, if covering 500 is present), or both. The filler may help accelerate sealing against PV leak, for example by reducing clotting time, particularly if covering 500 is permeable to water. As described above in connection with FIGS. 5A-F, a variety of stitches 510 and configurations of covering 500 may be used for sealing ring 350. It should be noted that if the filler takes the form of a metal or other abrasive material, a buffer material (such as fabric) may be appropriate to include to reduce the possibility that the filler will the tube 400 will fret against one another.

Each embodiment of sealing ring 350 shown in FIGS. 6A-6D includes tube 400, covering 500, outer filler 610, and one or more connections 510 connecting covering 500 and/or outer filler 610 to tube 400 and/or the stent 302 of valve 300. Outer filler 610 refers to filler that is positioned between tube 400 and covering 500. In FIG. 6A, covering 500 surrounds the entire cross-section of tube 400 and one stitch 510 connects each edge of covering 500 to the stent 302. Outer filler 610 is positioned between tube 400 and covering 500 and surrounds the cross-section of tube 400. In FIG. 6B, covering 500 surrounds the entire cross-section of tube 400, and one stitch 510 connects each edge of covering 500 to stent 302 and tube 400. Outer filler 610 is positioned between tube 400 and covering 500 and surrounds the cross-section of tube 400. In FIG. 6C, one edge of covering 500 is connected to both stent 302 and tube 400 with a first stitch 510, the other edge of covering 500 is connected to tube 400 with a second stitch 510, and the covering 500 does not cover the entire cross-section of tube 400. Similarly, the outer filler 610 is positioned between tune 400 and covering 500 and does not surround the entire cross-section of tube 400. In FIG. 6D, one stitch 510 connects a first edge of covering 500 to stent 302, another stitch 510 connects the other edge of covering 500 to tube 400, and covering 500 does not surround the entire cross-section of tube 400. Similarly, outer filler 610 is positioned between tube 400 and covering 500 and does not surround the entire cross-section of tube 400.

FIGS. 6E-H correspond to FIGS. 6A-D, respectively, with the exception that in addition to an outer filler 610, the sealing rings 350 of FIGS. 6E-H include an inner filler 620. Inner filler 620 refers to filler that is positioned substantially or completely within tube 400. Otherwise, the patterns of covering 500 and stitches 510 are identical between FIGS. 6A-D and 6E-H, respectively.

FIGS. 6I-L correspond to FIGS. 6E-H, respectively, with the exception that outer filler 610 is absent and only inner filler 620 is present. Otherwise, the patterns of covering 500 and stitches 510 are identical between FIGS. 6E-H and 6I-L, respectively.

In FIG. 6M, one edge of covering 500 is stitched to stent 302, and covering 500 does not surround the entire cross-section of tube 400. Inner filler 620 is positioned within tube 400. This generally corresponds to sealing ring 350 of FIG. 5A with an inner filler 620. In FIG. 6N, one edge of covering 500 is connected to both stent 302 and tube 400 by a single stitch 510, and the covering 500 does not surround the entire cross-section of tube 400. Inner filler 620 is positioned within tube 400. This generally corresponds to sealing ring 350 of FIG. 5C with an inner filler 620. In FIG. 6O, covering 500 is absent and a single stitch 510 attaches tube 400 to stent 300, with inner filler 620 positioned within tube 400. In this embodiment, it is important that inner filler 620 and tube 400 be chosen such that inner filler 620 cannot escape tube 400.

As described in connection with sealing rings 350 illustrated in FIGS. 5A-F, any covering 500 used in connection with filler may surround the entire cross-section of tube 400 or only a portion thereof. The same is true of outer filler 610. Further, as described above with reference to FIGS. 5A-F, the orientation of covering 500 may be reversed so that the covering 500 covers only a distal portion of tube 400. In embodiments in which covering 500 has this reverse orientation, outer filler 610 may also have a similar reverse orientation.

Figure 7A:
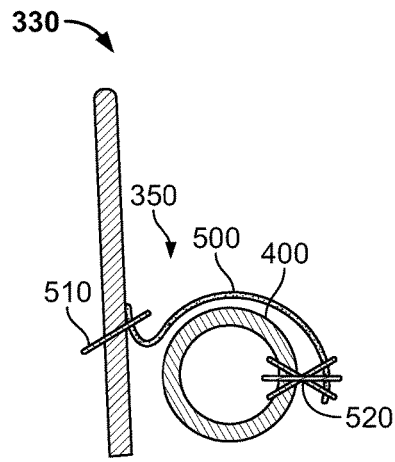
FIGS. 7A-P are highly schematic cross sectional views of a portion of a prosthetic heart valve with a sealing ring having a tacking stitch.
Figure 7B:
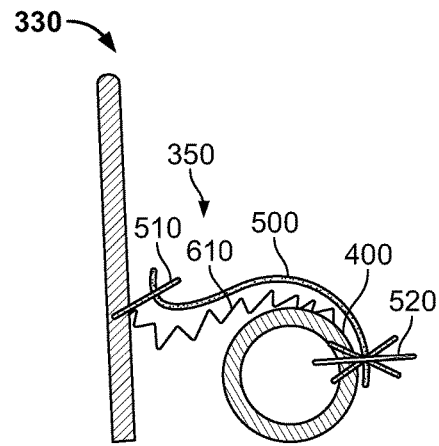
Figure 7C:
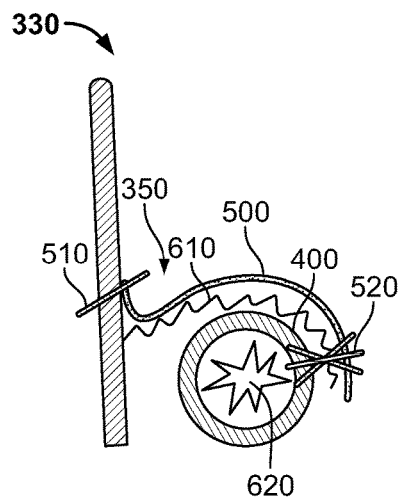

As described above the tube 400 may not change shapes as expected if covering 500 is tightly wrapped around and connected to tube 400. This may be particularly true of a tube 400 formed of a braided mesh. One way of mitigating this potential problem is, as described above, reducing or eliminating the number of stitches 500 directly connecting covering 500 to tube 400. However, another solution is the use of tacking stitching 520 or expandable stitching 530. Tacking stitching 520, illustrated in FIGS. 7A-P, generally refers to the use of intermittent stitching along the circumference of stent 302 holding the stitched material loosely in place. Expandable stitching 530, illustrated in FIGS. 8A-P, generally refers to stitching that allows for seam expansion. Expandable stitching 530 may be accomplished, for example, with the use of a very loose stitch or with a stitch sewn with an elastic material, such as thread formed from silicone.

Figure 7D:
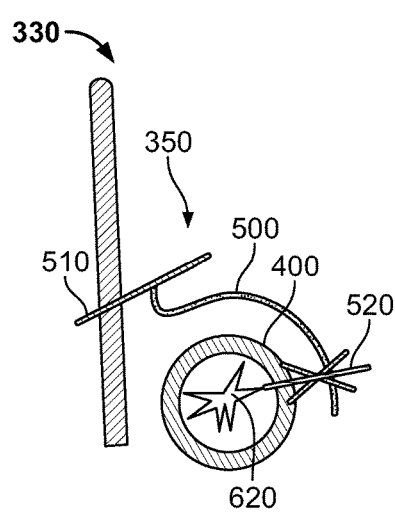
Figure 7E:
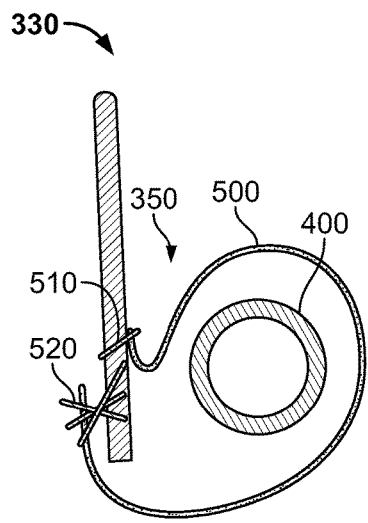
Figure 7F:
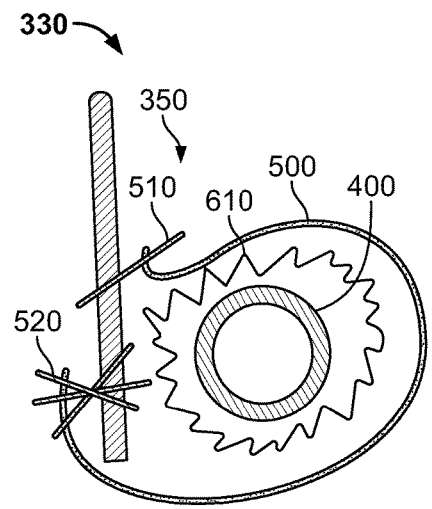
Figure 7G:
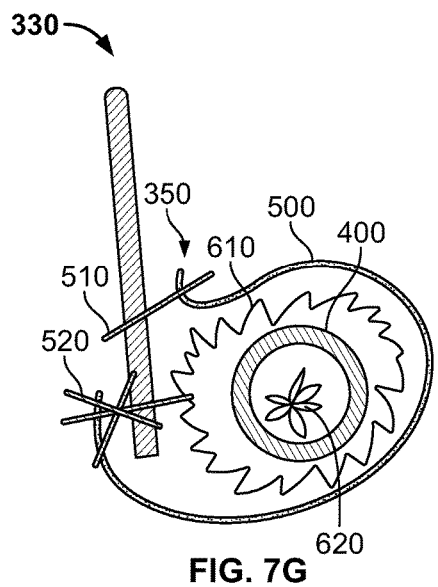

For example, FIGS. 7A-D illustrate sealing ring 350 with covering 500 attached at a first edge to stent 302 with a first stitch 510 and at a second edge to tube 500 with a tacking stitch 520, represented in the figures by a line with a cross through the line. The covering 500 does not fully cover the cross-section of tube 400, nor does the outer filler 610, where present. FIGS. 7A-D illustrate embodiments of sealing ring 350 with no filler (FIG. 7A), outer filler 610 (FIG. 7B), outer filler 610 and inner filler 620 (FIG. 7C), and inner filler 620 (FIG. 7D).

Figure 7H:
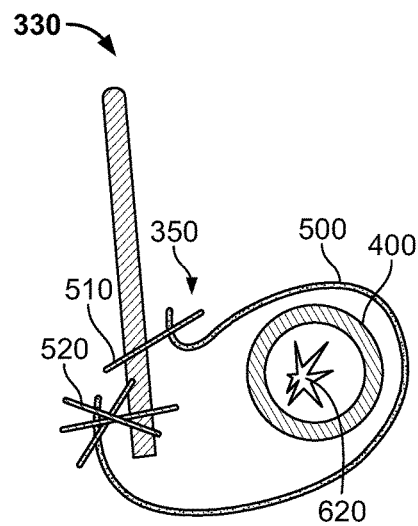
Figure 7I:
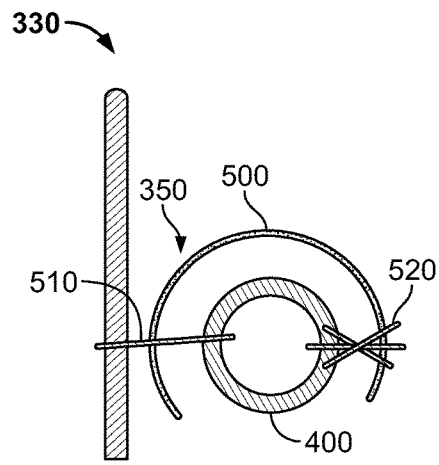
Figure 7J:
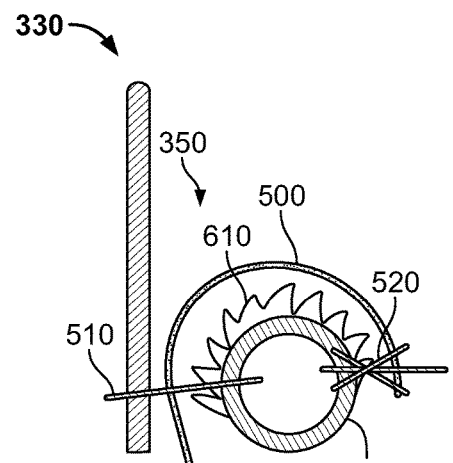
Figure 7K:
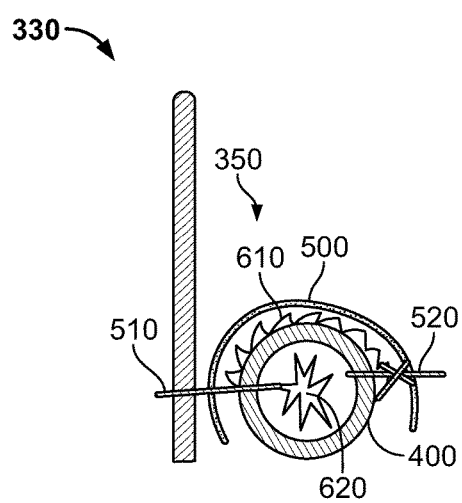

FIGS. 7E-H illustrate sealing ring 350 with covering 500 attached at a first edge to stent 302 with a stitch 510 and at a second edge to stent 302 with a tacking stitch 520. The covering 500 fully covers the cross-section of tube 400, as does the outer filler 610, where present. FIGS. 7E-H illustrate embodiments of sealing ring 350 with no filler (FIG. 7E), outer filler 610 (FIG. 7F), outer filler 610 and inner filler 620 (FIG. 7G), and inner filler 620 (FIG. 7H).

Figure 7L:
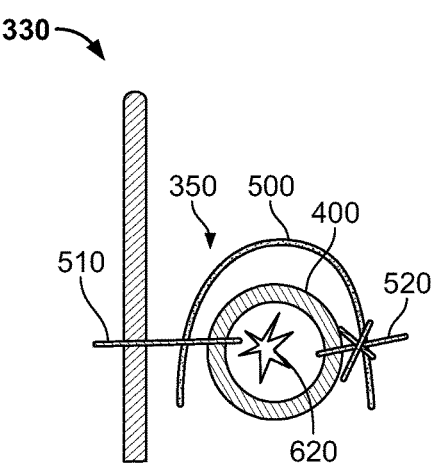
Figure 7M:
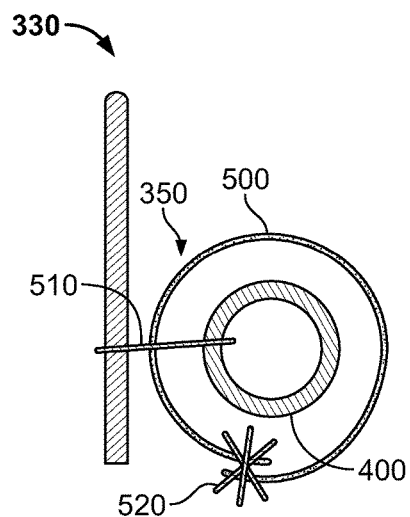
Figure 7N:
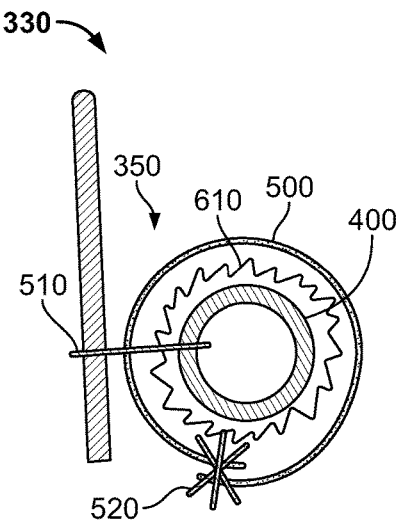
Figure 7O:
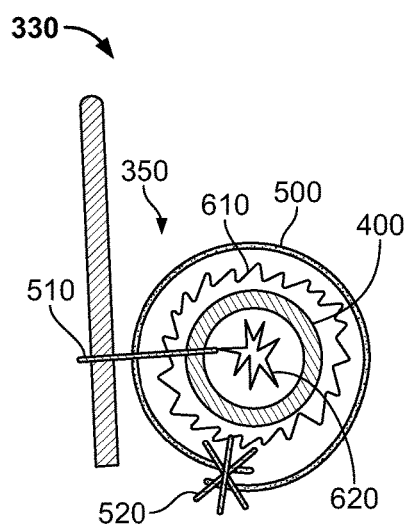

FIGS. 7I-L illustrate sealing ring 350 with covering 500 attached at a first edge to stent 302 and tube 400 with a stitch 510 and at a second edge to tube 400 with a tacking stitch 520. The covering 500 does not fully cover the cross-section of the tube 400, nor does the outer filler 610, where present. FIGS. 7I-L illustrate embodiments of sealing ring 350 with no filler (FIG. 7I), outer filler 610 (FIG. 7J), outer filler 610 and inner filler 620 (FIG. 7K), and inner filler 620 (FIG. 7L).

Figure 7P:
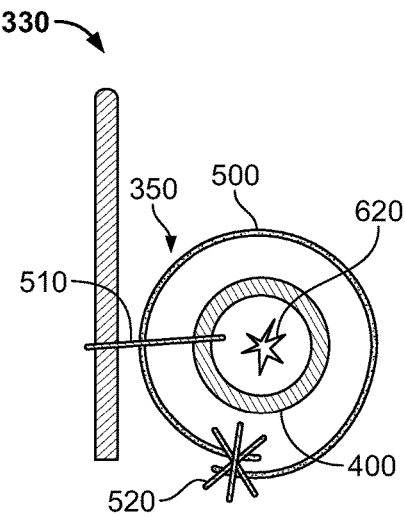

FIGS. 7M-P illustrate sealing ring 350 with covering 500 attached to stent 302 and tube 400 with a stitch 500, with both edges of covering 500 attached to one another and tube 400 with a tacking stitch 520. The covering 500 fully covers the cross-section of the tube 400, as does the outer filler 610, where present. FIGS. 7M-P illustrate embodiments of sealing ring 350 with no filler (FIG. 7M), outer filler 610 (FIG. 7N), outer filler 610 and inner filler 620 (FIG. 7O), and inner filler 620 (FIG. 7P).

Figure 8A:
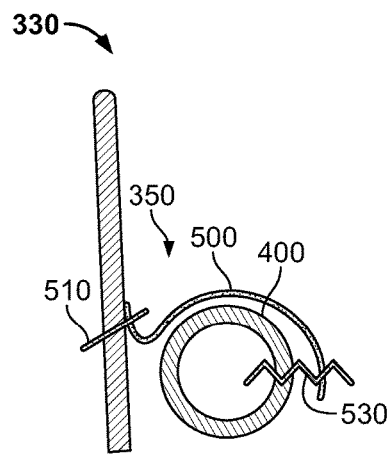
FIGS. 8A-P are highly schematic cross sectional views of a portion of a prosthetic heart valve with a sealing ring having an expandable stitch.
Figure 8B:
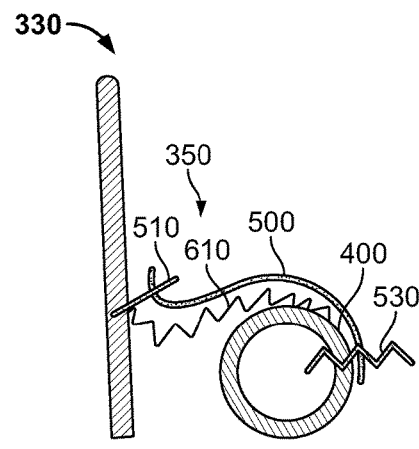
Figure 8C:
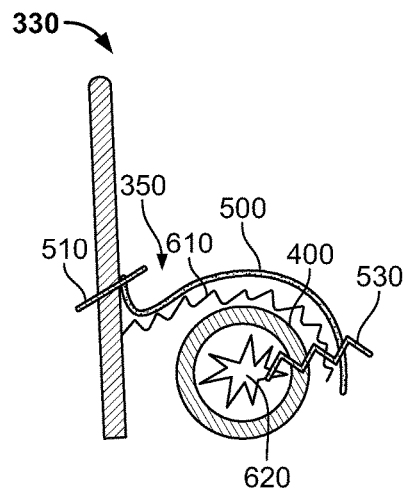
Figure 8D:
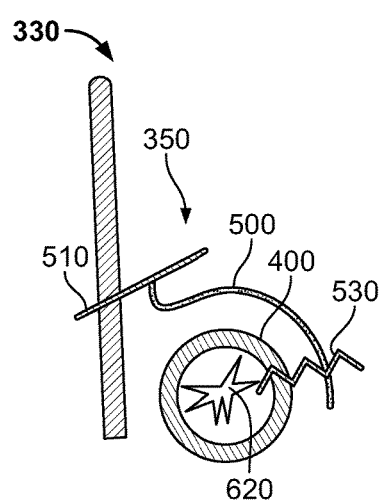
Figure 8E:
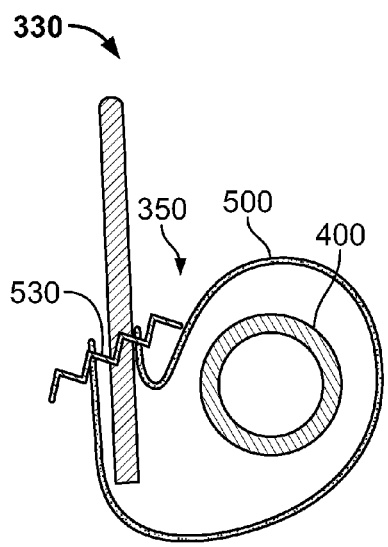
Figure 8F:
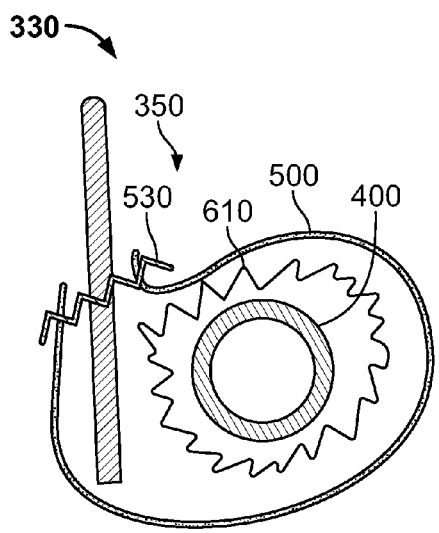
Figure 8G:
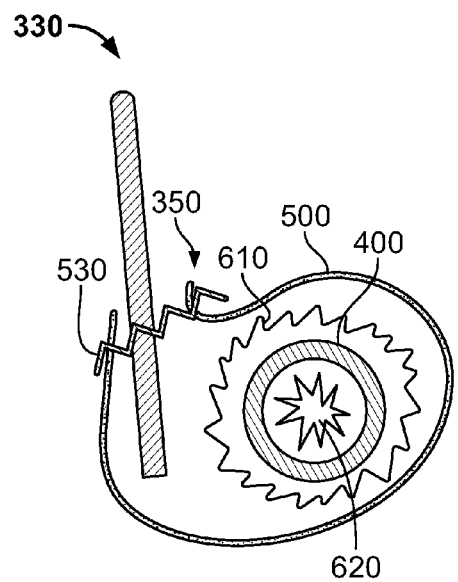
Figure 8H:
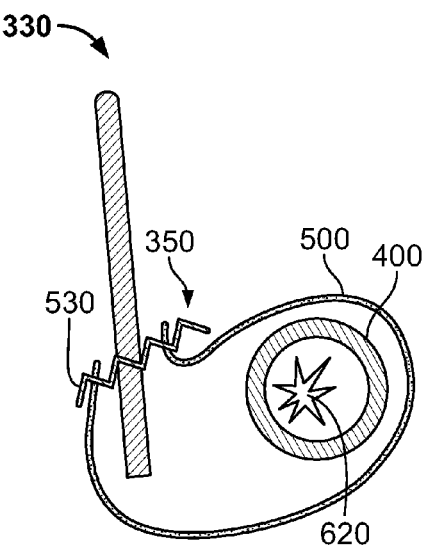
Figure 8I:
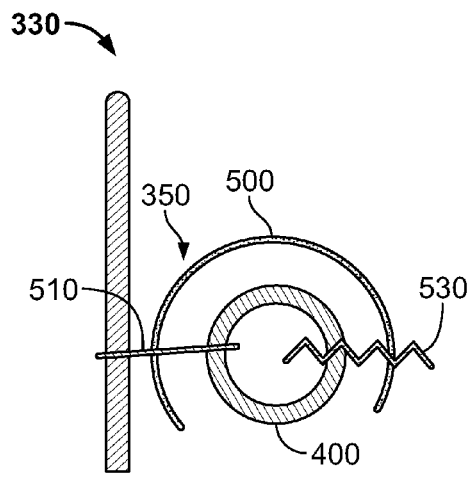
Figure 8J:
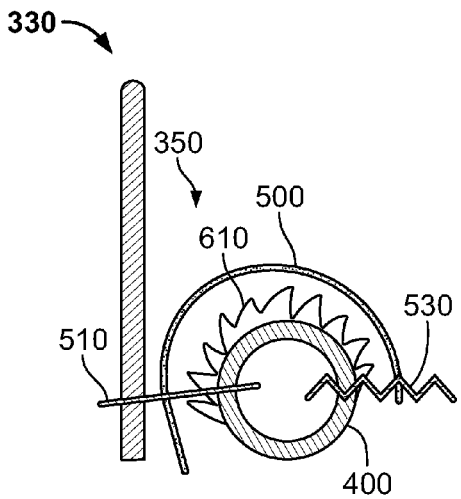
Figure 8K:
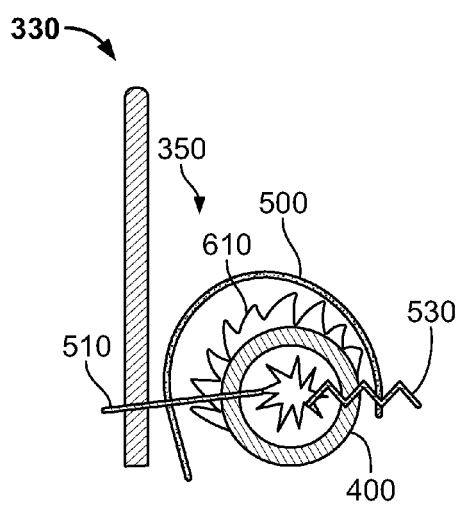
Figure 8L:
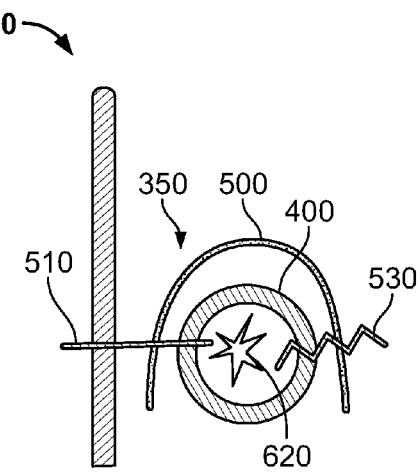
Figure 8M:
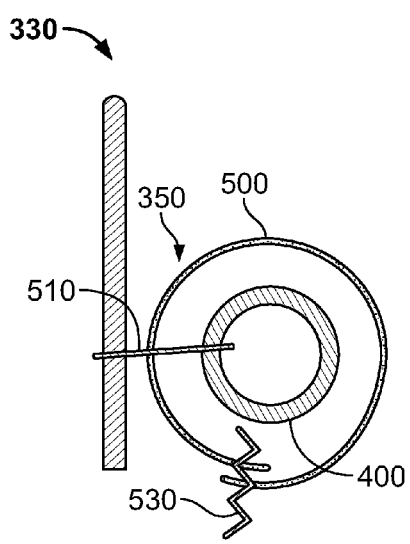
Figure 8N:
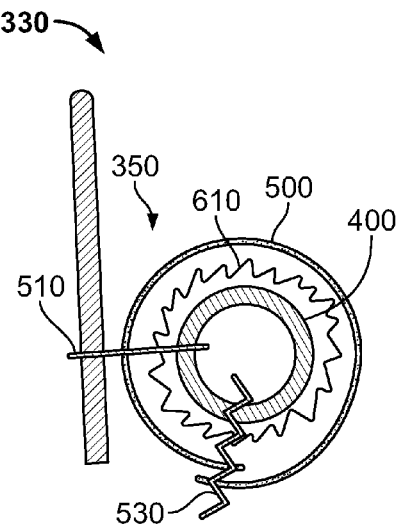
Figure 8O:
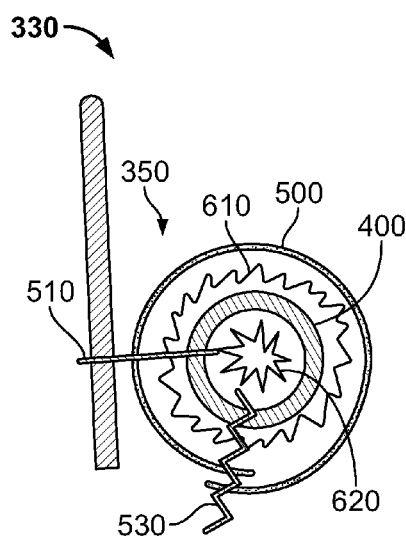
Figure 8P:
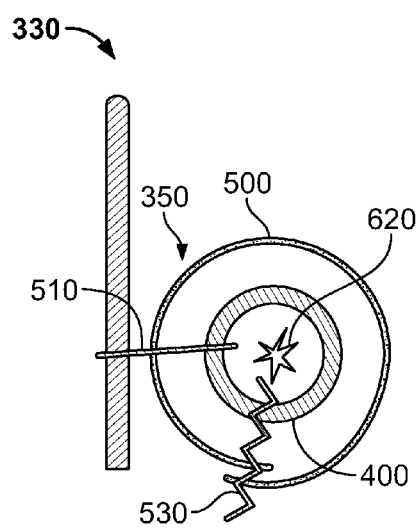

FIGS. 8A-8P illustrate embodiments of sealing ring 350 using an expandable stitch 530. FIGS. 8A-D illustrate sealing ring 350 with covering 500 attached at a first edge to stent 302 with a stitch 510 and at a second edge to tube 500 with an expandable stitch 530, represented in the figures by a line with a zigzag pattern along the line. The covering 500 does not fully cover the cross-section of tube 400, nor does the outer filler 610, where present. FIGS. 8A-D illustrate embodiments of sealing ring 350 with no filler (FIG. 8A), outer filler 610 (FIG. 8B), outer filler 610 and inner filler 620 (FIG. 8C), and inner filler 620 (FIG. 8D).

FIGS. 8E-H illustrate sealing ring 350 with covering 500 with an expandable stitch 530 attaching both edges of the covering 500 to one another and the stent 302. The covering 500 fully covers the cross-section of tube 400, as does the outer filler 610, where present. FIGS. 8E-H illustrate embodiments of sealing ring 350 with no filler (FIG. 8E), outer filler 610 (FIG. 8F), outer filler 610 and inner filler 620 (FIG. 8G), and inner filler 620 (FIG. 8H).

FIGS. 8I-L illustrate sealing ring 350 with covering 500 attached at a first edge to stent 302 and tube 400 with a stitch 510 and at a second edge to tube 400 with an expandable stitch 530. The covering 500 does not fully cover the cross-section of the tube 400, nor does the outer filler 610, where present. FIGS. 8I-L illustrate embodiments of sealing ring 350 with no filler (FIG. 8I), outer filler 610 (FIG. 8J), outer filler 610 and inner filler 620 (FIG. 8K), and inner filler 620 (FIG. 8L).

FIGS. 8M-P illustrate sealing ring 350 with covering 500 attached to stent 302 and tube 400 with a stitch 500, with both edges of covering 500 attached to one another and tube 400 with an expandable stitch 530. The covering 500 fully covers the cross-section of the tube 400, as does the outer filler 610, where present. FIGS. 8M-P illustrate embodiments of sealing ring 350 with no filler (FIG. 8M), outer filler 610 (FIG. 8N), outer filler 610 and inner filler 620 (FIG. 8O), and inner filler 620 (FIG. 8P).

Figure 9A:
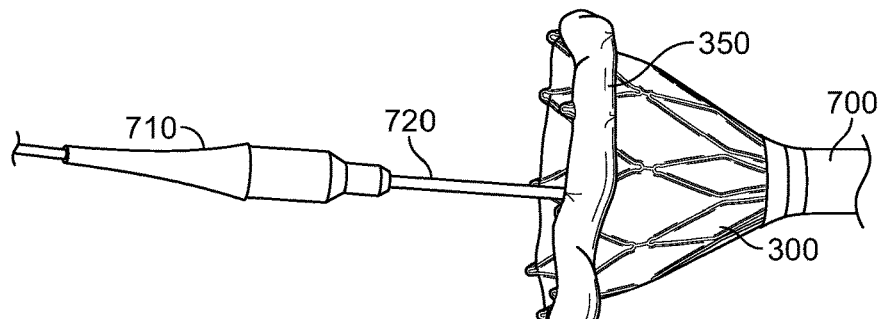
FIGS. 9A-E illustrate a prosthetic heart valve at different stages of resheathing into a delivery device.
Figure 9B:
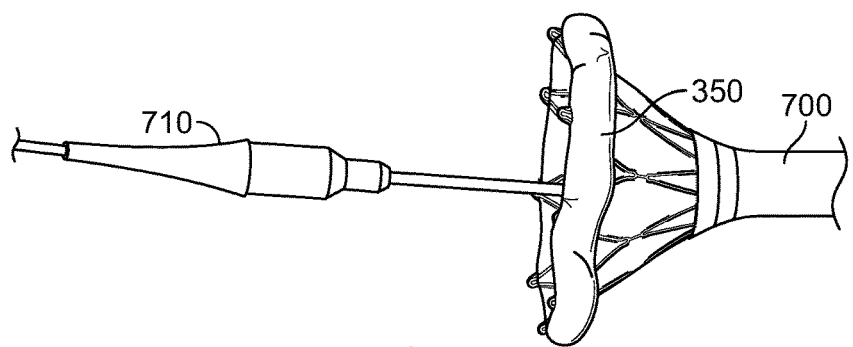
Figure 9C:
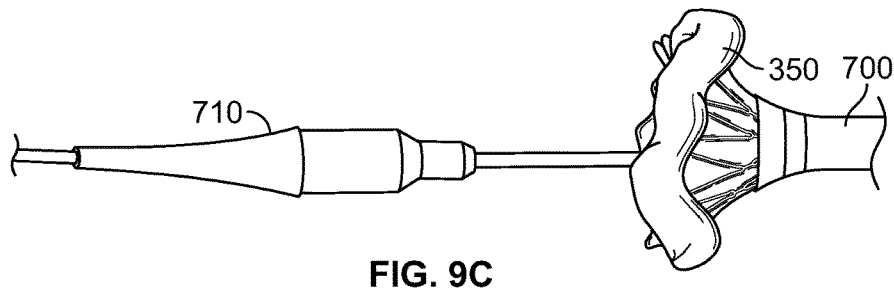
Figure 9D:
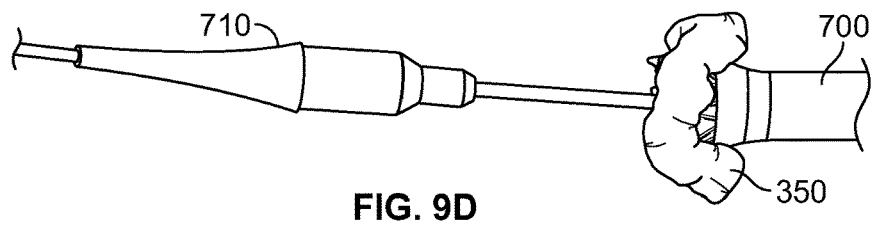
Figure 9E:
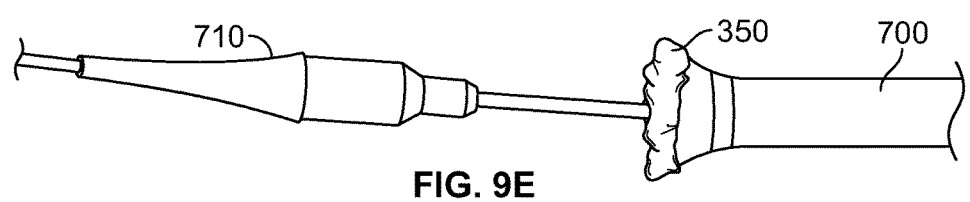

FIGS. 9A-E illustrate side views of prosthetic heart valve 300 being resheathed into a delivery device (heart valve 300 only labeled in FIG. 9A). Briefly, the delivery device includes an outer sheath 700, a distal tip 710, and an inner sheath 720 (inner sheath 720 labeled only in FIG. 9A). In this embodiment, sealing ring 350 takes the form of a tube 400 formed of a Nitinol coil with a diamond shape 420. The sealing ring 350 is on the left end of the prosthetic valve 300 as illustrated. As noted above, prosthetic heart valve may be resheathable. For example, during delivery, a user may first allow prosthetic heart valve 300 to partially expand outside of outer sheath 700 to test positioning and functioning of the valve (FIG. 9A) prior to fully releasing the valve. FIGS. 7A-E illustrate different levels of resheathing, with greater resheathing progressing from FIG. 9A to FIG. 9E. As described above with respect to FIGS. 4A-B, the rectangular shape 410 or diamond shape 420 of a coiled wire forming tube 400 may allow for the tube 400 to collapse to a reduced profile during loading or resheathing the valve 300 into the delivery device. As can be seen in the illustrations, particularly from FIG. 9B to FIG. 9D, during loading or resheathing, the tube rectangular shape 410 or diamond shape 420 of the coiled wire may allow the tube 400 to fold away from the remainder of valve 300 during the process. In addition to collapsing during resheathing (or loading), the sealing ring 350, and in particular the tube 400, may pivot or rotate with respect to inflow end 330 of the valve 300. This is best illustrated in FIGS. 9D-E, in which the inflow end 330 enters the outer sheath 700 as the sealing ring 350 is forced to pivot or rotate away from the end of distal sheath 700. For example, the entirety or nearly the entirety of inflow end 330 may be positioned within outer sheath 700 prior to any of sealing ring 350 entering outer sheath 700 during a resheathing (or loading) process. As such, when fully loaded into the delivery device, the tube 400 may be completely or substantially axially offset from the remainder of prosthetic heart valve 300, including the leaflet belly B regions, reducing the crimping profile even further.

Although certain embodiments of the prosthetic heart valve described herein may provide a single feature for reducing para valvular leakage, it should be understood that multiple similar or dissimilar features may be utilized on a single prosthetic heart valve to reduce para valvular leak. For example, one or more sealing rings may be used on a single prosthetic heart valve, including a first sealing ring disposed proximal to (or within) the native valve annulus and a second sealing ring disposed distal the first sealing ring. In other examples, a sealing ring may be disposed proximal to (or within) the native valve annulus, and one or more pockets expandable upon retrograde blood flow may be disposed distal the sealing ring. Prosthetic heart valves with expandable pockets are described in greater detail in U.S. Patent Publication No. 2011/0098802, the disclosure of which is hereby incorporated by reference herein.

In one embodiment of the disclosure, a prosthetic heart valve comprises: a collapsible and expandable stent extending from an inflow end to an outflow end; a plurality of prosthetic valve leaflets coupled to the stent, each leaflet having a leaflet belly; and a sealing ring coupled to the inflow end of the stent, the sealing ring comprising a tube extending circumferentially around the inflow end of the stent, the sealing ring being axially offset from the leaflet belly when the stent is in a collapsed condition, wherein the tube is formed from a wire coiled into a repeating shape such that the tube is collapsible; and/or the wire is coiled into a rectangular shape; and/or the wire is coiled into a diamond shape having a major axis and a minor axis; and/or the major axis is approximately 3 mm and the minor axis is approximately 2 mm; and/or the major axis is approximately 4 mm and the minor axis is approximately 2 mm; and/or the major axis is approximately 4 mm and the minor axis is approximately 3 mm; and/or the wire has a thickness of between approximately 0.05 mm and approximately 0.175 mm; and/or the wire has a thickness and there is a distance between adjacent repeating shapes of the coiled wire, a ratio of the thickness to the distance being between approximately 1:6 and approximately 1:32.

In another embodiment of the disclosure, a prosthetic heart valve comprises: a collapsible and expandable stent extending from an inflow end to an outflow end; a plurality of prosthetic valve leaflets coupled to the stent, each leaflet having a leaflet belly; and a sealing ring coupled to the inflow end of the stent, the sealing ring comprising a tube extending circumferentially around the inflow end of the stent, a covering at least partially surrounding the tube, and at least one of a first filler positioned within the tube and a second filler positioned between the tube and the covering, the sealing ring being axially offset from the leaflet belly when the stent is in a collapsed condition; and/or the covering is formed from a material selected form the group consisting of tissues, fabrics, and polymers; and/or at least one of the first filler and the second filler is formed from a material selected from the group consisting of metals, tissues, fabrics, polymers, and water-swellable materials; and/or at least one of the first filler and the second filler is configured to expand upon exposure to blood.

In a further embodiment of the disclosure, a prosthetic heart valve comprises: a collapsible and expandable stent extending from an inflow end to an outflow end; a plurality of prosthetic valve leaflets coupled to the stent, each leaflet having a leaflet belly; and a sealing ring coupled to the inflow end of the stent, the sealing ring comprising a tube extending circumferentially around the inflow end of the stent and a covering at least partially surrounding the tube, the sealing ring being axially offset from the leaflet belly when the stent is in a collapsed condition, wherein the covering has a first edge and a second edge, the first end coupled to the stent by a first thread; and/or the first thread couples the first edge of the covering and the tube to the stent; and/or a second thread coupling the second edge of the covering to the tube; and/or the second thread is formed of an elastic material; and/or the first thread couples the second edge of the covering to the first edge of the covering and the stent; and/or the first thread is formed of an elastic material; and/or the elastic material is silicone.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims. Such modification may include, for example, combining of certain elements of one embodiment of the disclosure with other elements of another embodiment of the disclosure.

The invention claimed is:

1. A method of delivering a prosthetic heart valve to a patient comprising:
    loading the prosthetic heart valve into an outer sheath of a delivery device in a collapsed condition, the prosthetic heart valve including a collapsible and expandable stent extending from an inflow end to an outflow end, a plurality of valve leaflets coupled to the stent, and a sealing ring coupled to the stent adjacent the inflow end, the sealing ring including a tube;
    advancing the delivery device to a native valve annulus of the patient; and
    fully deploying the prosthetic heart valve from the outer sheath and into the native valve annulus so that the prosthetic heart valve transitions from the collapsed condition to an expanded condition;
    wherein the tube has a profile that increases from a reduced profile to an enlarged profile as the prosthetic heart valve transitions from the collapsed condition to the expanded condition.

2. The method of claim 1, wherein the valve leaflets include a leaflet belly and the sealing ring is axially offset from the leaflet belly while the prosthetic heart valve is maintained in the collapsed condition by the outer sheath.

3. The method of claim 2, wherein after the prosthetic valve is fully deployed from the outer sheath, the sealing ring axially overlaps the leaflet belly.

4. The method of claim 1, wherein the tube includes a wire coiled into a repeating shape.

5. The method of claim 4, wherein the wire is formed of a shape-memory alloy.

6. The method of claim 5, wherein the tube has the enlarged profile in the absence of applied forces.

7. The method of claim 4, wherein the wire is coiled into a rectangular shape.

8. The method of claim 4, wherein the wire is coiled into a diamond shape having a major axis and a minor axis.

9. The method of claim 8, wherein the major axis is approximately 3 mm and the minor axis is approximately 2 mm when the prosthetic heart valve is in the expanded condition.

10. The method of claim 1, further comprising the step of partially deploying the prosthetic heart valve from the outer sheath so that the sealing ring has the enlarged profile and is positioned in the native valve annulus, while the outflow end of the stent remains in the outer sheath of the delivery device.

11. The method of claim 10, further comprising testing at least one of a position and a function of the prosthetic heart valve after partially deploying the prosthetic heart valve and prior to fully deploying the prosthetic heart valve.

12. The method of claim 11, further comprising resheathing the prosthetic valve into the outer sheath of the delivery device so that the tube has the reduced profile, after testing the prosthetic heart valve.

13. The method of claim 12, wherein the tube of the sealing ring pivots away from the inflow end of the stent during the resheathing step.

14. The method of claim 1, wherein the tube extends circumferentially around the inflow end of the stent and a covering at least partially surrounds the tube.

15. The method of claim 14, wherein the covering is formed from a material selected form the group consisting of tissues, fabrics, and polymers.

16. The method of claim 14, wherein a first filler is positioned within the tube.

17. The method of claim 16, wherein the first filler is formed from a material selected from the group consisting of metals, tissues, fabrics, polymers, and water-swellable materials.

18. The method of claim 17, wherein, following full deployment of the prosthetic valve from the outer sheath, the first filler expands upon exposure to blood.

19. The method of claim 16, wherein a second filler is positioned between the tube and the covering.

20. The method of claim 14, wherein a first filler is positioned between the tube and the covering.

* * * * *